(12) United States Patent
Chevillet et al.

(10) Patent No.: US 12,133,728 B2
(45) Date of Patent: Nov. 5, 2024

(54) SYSTEMS AND METHODS FOR EVALUATING TISSUE OF A SUBJECT

(71) Applicants: University of Washington, Seattle, WA (US); Fred Hutchinson Cancer Research Center, Seattle, WA (US)

(72) Inventors: John R. Chevillet, Seattle, WA (US); Tatiana D. Khokhlova, Seattle, WA (US); George R. Schade, Seattle, WA (US); Joo Ha Hwang, Bellevue, WA (US); Muneesh Tewari, Seattle, WA (US)

(73) Assignees: UNIVERSITY OF WASHINGTON, Seattle, WA (US); FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 18/094,206

(22) Filed: Jan. 6, 2023

(65) Prior Publication Data

US 2024/0041358 A1    Feb. 8, 2024

Related U.S. Application Data

(63) Continuation of application No. 16/936,095, filed on Jul. 22, 2020, now abandoned, which is a (Continued)

(51) Int. Cl.
*A61B 5/145* (2006.01)
*A61B 5/00* (2006.01)
(Continued)

(52) U.S. Cl.
CPC .......... *A61B 5/14546* (2013.01); *A61B 5/145* (2013.01); *A61B 5/14507* (2013.01); (Continued)

(58) Field of Classification Search
CPC ... A61B 5/145; A61B 5/14507; A61B 5/4836; A61B 5/14546; A61B 5/15; A61B 8/08;
(Continued)

(56) References Cited

U.S. PATENT DOCUMENTS 6,589,173 B1    7/2003    Mitragotri
6,824,516 B2    11/2004   Batten et al.
(Continued)

FOREIGN PATENT DOCUMENTS

CN    103025890 A    *    4/2013    ........... C12Q 1/6886
WO    2009094554 A2        7/2009
(Continued)

OTHER PUBLICATIONS

AACR. Liquid Biopsy Workshop Session II transcript.
(Continued)

*Primary Examiner* — Chao Sheng
(74) *Attorney, Agent, or Firm* — Perkins Coie LLP

(57) ABSTRACT

The present disclosure is directed to relates to systems and methods for evaluating tissue using high intensity focused ultrasound (HIFU) energy. In one embodiment, for example, a system for treating a patient comprises an ultrasound source configured to deliver HIFU energy to a target tissue mass of the patient and a function generator operably coupled to the ultrasound source for initiating a pulsing protocol for delivering the HIFU energy. The system further comprises a controller configured to perform operations comprising applying HIFU energy to induce cavitation in the target tissue mass and cause a biomarker to be released, comparing a baseline concentration of the biomarker from a first fluid sample to a concentration of the biomarker in a second fluid sample within 2 hours after applying HIFU, and
(Continued)

repeating the applying and comparing until the concentration of the biomarker in the fluid sample falls below a threshold value.

18 Claims, 10 Drawing Sheets

Specification includes a Sequence Listing.

Related U.S. Application Data continuation of application No. 15/122,394, filed as application No. PCT/US2015/024144 on Apr. 2, 2015, now abandoned.

(60) Provisional application No. 62/072,915, filed on Oct. 30, 2014, provisional application No. 61/974,317, filed on Apr. 2, 2014.

(51) Int. Cl.
| | |
|---|---|
| *A61B 5/15* | (2006.01) |
| *A61B 8/08* | (2006.01) |
| *A61B 10/00* | (2006.01) |
| *A61N 7/02* | (2006.01) |
| *C12Q 1/6886* | (2018.01) |

(52) U.S. Cl.
CPC .............. *A61B 5/15* (2013.01); *A61B 5/4836* (2013.01); *A61B 8/08* (2013.01); *A61B 8/5223* (2013.01); *A61B 10/0038* (2013.01); *A61B 10/007* (2013.01); *A61N 7/022* (2013.01); *C12Q 1/6886* (2013.01); *A61B 2010/0077* (2013.01); *A61N 7/02* (2013.01); *C12Q 2600/118* (2013.01); *C12Q 2600/158* (2013.01)

(58) Field of Classification Search
CPC . A61B 8/5223; A61B 10/0038; A61B 10/007; A61B 2010/0077; A61N 7/022; A61N 7/02; C12Q 1/6886; C12Q 2600/118; C12Q 2600/158

See application file for complete search history.

(56) References Cited

U.S. PATENT DOCUMENTS

| | | | |
|---|---|---|---|
| 8,278,053 | B2 | 10/2012 | Glazer et al. |
| 2003/0233045 | A1 | 12/2003 | Vaezy et al. |
| 2005/0043726 | A1 | 2/2005 | McHale et al. |
| 2007/0244568 | A1 | 10/2007 | Matsuda |
| 2008/0183200 | A1 | 7/2008 | Babaev et al. |
| 2008/0319356 | A1 | 12/2008 | Cain et al. |
| 2009/0036774 | A1 | 2/2009 | Weng et al. |
| 2009/0269317 | A1 | 10/2009 | Davalos |
| 2010/0009400 | A1* | 1/2010 | Glazer ............... G01N 33/5082 435/29 |
| 2010/0092424 | A1 | 4/2010 | Sanghvi et al. |
| 2010/0191157 | A1 | 7/2010 | Sanghvi |
| 2010/0228122 | A1 | 9/2010 | Keenan et al. |
| 2010/0241005 | A1 | 9/2010 | Darlington |
| 2010/0261176 | A1 | 10/2010 | Mitragotri et al. |
| 2011/0054315 | A1 | 3/2011 | Roberts et al. |
| 2011/0059053 | A1 | 3/2011 | Chaunhan |
| 2011/0251528 | A1* | 10/2011 | Canney ..................... A61N 7/02 601/3 |
| 2012/0010541 | A1 | 1/2012 | Cain et al. |
| 2012/0259250 | A1 | 10/2012 | Sapozhnikov et al. |
| 2013/0018260 | A1* | 1/2013 | Sanghvi .................. A61B 18/04 600/438 |
| 2013/0041293 | A1 | 2/2013 | Cain et al. |
| 2013/0066240 | A1 | 3/2013 | Van Heesch et al. |
| 2013/0171653 | A1 | 7/2013 | Doll et al. |
| 2013/0225994 | A1 | 8/2013 | Hsu et al. |
| 2013/0237780 | A1 | 9/2013 | Beasley |
| 2014/0350677 | A1 | 11/2014 | Chang et al. |
| 2015/0119763 | A1 | 4/2015 | Canney et al. |
| 2015/0153909 | A1 | 6/2015 | Zubas et al. |
| 2017/0071515 | A1 | 3/2017 | Chevillet et al. |
| 2017/0072228 | A1 | 3/2017 | Wang et al. |
| 2021/0038924 | A1 | 2/2021 | Wang et al. |

FOREIGN PATENT DOCUMENTS

| | | |
|---|---|---|
| WO | 2012162133 A1 | 11/2012 |
| WO | 2015153441 A1 | 10/2015 |
| WO | 20150153909 A2 | 10/2015 |

OTHER PUBLICATIONS

Albertsen, PC , "PSA testing: public policy or private penchant?", (Translated from eng) Jama 296(19):2371-2373, 2006.
Arroyo, JD et al., "Argonaute2 complexes carry a population of circulating microRNAs independent of vesicles in human plasma", Proc Natl Acad Sci U S A 108(12):5003-5008 (in eng), 2011.
Aus, G. , "Current status of HIFU and cryotherapy in prostate cancer—a review", (Translated from eng) Eur Urol 50(5):927-934; discussion 934, 2006.
Baldwin, K. , "Liquid Biopsy May Help Guide Treatment Decisions for Advanced Solid Tumors", ASCO Press Release. Jun. 4, 2016.
Baughman, D. et al., "Exosome Diagnostics Launches World's First Exosomal RNA-Based Liquid", Biopsy, ExoDx™ Lung(ALK). Jan. 21, 2016. http://www.exosomedx.com/news-events/press-releases/exosome-diagnostics-launches-worlds-first-exosomal-rna-based-liquid-biopsy.
Belcher, K. , "Therapy Monitoring Emerges as a Promising Application for Liquid Biopsy", Frost & Sullivan Press Release, Jan. 15, 2016., Accessed at http://ww2.frost.com/news/press-releases/majority-users-identify-therapy-monitoring-promising-liquid-biopsy-application/.
Bettegowda, C. et al., "Detection of Circulating Tumor DNA in Early- and Late-Stage Human Malignancies. Science Translational Medicine", Feb. 19, 2014:vol. 6, Issue 224, pp. 224ra24 DOI: 10.1126/scitranslmed.3007094.
Blount, LV et al., "Point mutations in the Ki-ras2 gene of codon 12 in the Dunning R-3327 Prostatic Adenocarcinoma system", (Translated from eng) Prostate 28(1):44-50, 1996.
Borboroglu, PG et al., "Extensive repeat transrectal ultrasound guided prostate biopsy in patients with previous benign sextant biopsies", (Translated from eng) J Urol 163(1):158-162, 2000.
Calin, GA et al., "A MicroRNA signature associated with prognosis and progression in chronic lymphocytic leukemia", (Translated from eng) N Engl J Med 353(17):1793-1801, 2005.
Canney, M.S. et al., "Tissue erosion using shock wave heating and millisecond boiling in HIFU fields.", AIP Conf. Proc. 2010, 1215, 36-39.
Canney, MS et al., "Shock-induced heating and millisecond boiling in gels and tissue due to high intensity focused ultrasound.", Utrasound Med. Biol. Feb. 2010; 36(2):250-67.
Childberg, M. , "Liquid Biopsy: What's in a Name?", Marty Chilberg's Instablog. May 17, 2015. Accessed at http://seekingalpha.com/instablog/400846-marty-chilberg/4008696-liquid-biopsy-whats-in-a-name.
Desmond-Hellmann, S. et al., "Toward precision medicine: a new social contract?", (Translated from eng) Sci Transl Med 4(129):129ed123, 2012.
Diehl, F. et al., "Circulating mutant DNA to assess tumor dynamics", (Translated from eng) Nat Med 14(9):985-990, 2008.
Diehl, F. et al., "Detection and quantification of mutations in the plasma of patients with colorectal tumors", (Translated from eng) Proc Natl Acad Sci U S A 102(45):16368-16373, 2005.
Djavan, B. et al., "Safety and morbidity of first and repeat transrectal ultrasound guided prostate needle biopsies: results of a prospective European prostate cancer detection study", (Translated from eng) J Urol 166(3):856-860, 2001.

(56) References Cited

OTHER PUBLICATIONS

Dubinsky, TJ et al., "High-intensity focused ultrasound: current potential and oncologic applications", (Translated from eng) AJR Am J Roentgenol 190(1):191-199, 2008.
Esquela-Kerscher, A. et al., "Oncomirs—microRNAs with a role in cancer", (Translated from eng) Nat Rev Cancer 6(4):259-269, 2006.
FDA Press Release. FDA approves first blood test to detect gene mutation associated with non-small cell lung cancer. Jun. 1, 2016. http://www.fda.gov/NewsEvents/Newsroom/PressAnnouncements/ucm504488.htm.
Final Office Action mailed Apr. 10, 2019 in U.S. Appl. No. 15/122,394 for Chevillet et al., filed Aug. 29, 2016, 40 pages.
Final Office Action mailed Apr. 22, 2020 in U.S. Appl. No. 15/122,394 for Chevillet et al., filed Aug. 29, 2016, 40 pages.
Final Office Action mailed Feb. 12, 2020 in U.S. Appl. No. 15/126,131 for Wang et al., filed Sep. 14, 2016, 26 pages.
Final Office Action mailed Jun. 1, 2023 in U.S. Appl. No. 16/927,860, 17 pages.
Final Office Action mailed Mar. 4, 2019 in U.S. Appl. No. 15/126,131 for Wang et al., filed Sep. 14, 2016, 30 pages.
Gerlinger, M. , "Intratumor heterogeneity and branched evolution revealed by multiregion sequencing", N Engl J Med. Mar. 8, 2012;366(10):883-92. doi: 10.1056/NEJMoa1113205. http://www.ncbi.nlm.nih.gov/pubmed/22397650.
Guardant Health press release. "Guardant Health Secures Series D Financing to Expand the Reach of its Digital Sequencing™ Platform in Oncology." Jan. 7. 2016., http://www.prnewswire.com/news-releases/guardant-health-secures-series-d-financing-toexpand-the-reach-of-its-digital-sequencing-platform-in-oncology-300200834.html.
Healthcare Bluebook accessed at http://www.healthcarebluebook.com.
HHHS. Principles for Codevelopment of an In Vitro Companion Diagnostic Device with a Therapeutic Product. Jul. 15, 2016:, Document 1400027 http://www.fda.gov/ucm/groups/fdagov-public/@fdagov-meddev-gen/documents/document/ucm510824.pdf.
Hindson, BJ et al., "High-throughput droplet digital PCR system for absolute quantitation of DNA copy number", (Translated from eng) Anal Chem 83(22):8604-8610, 2011.
Hu, Z. et al., "Investigation of HIFU-induced anti-tumor immunity in a murine tumor model," Journal of Translational Medicine 5, Article No. 34 (2007). Jul. 11, 2007.
Hwang, JH et al., "Correlation between inertial cavitation dose and endothelial cell damage in vivo", Translated from eng) Ultrasound Med Biol, 32(10):1611-1619, 2006.
Hwang, JH et al., "Current status of clinical high-intensity focused ultrasound", (Translated from eng) Conf Proc IEEE Eng Med Biol Soc 2009:130-133, 2009.
Hwang, JH et al., "High-intensity focused US: a potential new treatment for GI bleeding", (Translated from eng) Gastrointest Endosc 58(1):111-115, 2003.
Hwang, JH et al., "Targeted venous occlusion using pulsed high-intensity focused ultrasound", (Translated from eng) IEEE Trans Biomed Eng 57(1):37-40, 2010.
Hwang, JH et al., "Vascular effects induced by combined 1-MHz ultrasound and microbubble contrast agent treatments in vivo", (Translated from eng) Ultrasound Med Biol 31(4):553-564, 2005.
International Search Report and Written Opinion mailed Jan. 14, 2016, in International Application No. PCT/2015/024144, 16 pages.
International Search Report and Written Opinion mailed Jul. 2, 2015, in International Application No. PCT/US2015/023306, 6 pages.
Isaacs, JT et al., "Genetic instability coupled to clonal selection as a mechanism for tumor progression in the Dunning R-3327 rat prostatic adenocarcinoma system", (Translated from eng) Cancer Res 42(6):2353-2371, 1982.
Isaacs, JT et al., "The characterization of a newly identified, highly metastatic variety of Dunning R 3327 rat prostatic adenocarcinoma system: the MAT LyLu tumor", (Translated from eng) Invest Urol 19(1):20-23, 1981.

Jung, K. et al., "Plasma matrix metalloproteinase 9 as biomarker of prostate cancer progression in Dunning (Copenhagen) rats", (Translated from eng) Prostate 54(3):206-211, 2003.
Kennedy, JE , "High-intensity focused ultrasound in the treatment of solid tumours", (Translated from eng) Nat Rev Cancer 5(4):321-327 , 2005.
Keshavarzi et al. "Treatment of Uterine Fibroid Tumors in an In Situ Rat Model Using High-Intensity Focused Ultrasound", Fertility and Sterility, vol. 80, (Sep. 2003), pp. 761-767.
Khokhlova, T. et al., "Simulated Release of Nucleic Acid Cancer Biomarkers by HIFU: a Study in a Rat Prostate Cancer Model", 13th International Symposium on Therapeutic Ultrasound, May 13, 2013, 78.
Khokhlova, TD et al., "HIFU for palliative treatment of pancreatic cancer", Journal of Gastrointestinal Oncology., Sep. 2011, 175-184.
Kroh, EM et al., "Analysis of circulating microRNA biomarkers in plasma and serum using quantitative reverse transcription-PCR", (Translated from eng) Methods 50(4):298-301, 2010.
Leary, RJ et al., "Development of personalized tumor biomarkers using massively parallel sequencing", (Translated from eng) Sci Transl Med 2(20):20ra14, 2010.
Leon, SA et al., "Free DNA in the serum of cancer patients and the effect of therapy", Cancer Res. Mar. 1977;37(3):646-50.
Li, M. et al., "BEAMing up for detection and quantification of rare sequence variants", (Translated from eng) Nat Methods 3(2):95-97, 2006.
Misale, S. et al., "Emergence of KRAS mutations and acquired resistance to anti-EGFR therapy in colorectal cancer", Nature 486, 532-536 (2012).
Mitchell, PS et al., "Circulating microRNAs as stable blood-based markers for cancer detection", Proc Natl Acad Sci U S A 105(30):10513-10518, 2008.
Mukherjee, S. , "The Cancer Biopsy of the Future Could Be a Simple Blood Test", Fortune. Jun. 5, 2016. http://fortune.com/2016/06/05/asco-guardant-liquid-biopsy/.
NIH. Extracellular RNA Communication. May 19, 2016. http://commonfund.nih.gov/Exrna/index.
Non-Final Office Action mailed Aug. 16, 2019 in U.S. Appl. No. 15/126,131 for Wang et al., filed Sep. 14, 2016, 24 pages.
Non-Final Office Action mailed Jul. 8, 2022 in U.S. Appl. No. 16/936,095, 31 pages.
Non-Final Office Action mailed Nov. 20, 2018 in U.S. Appl. No. 15/126,131 for Wang et al., filed Sep. 14, 2016, 36 pages.
Non-Final Office Action mailed Oct. 31, 2018 in U.S. Appl. No. 15/122,394 for Chevillet et al., filed Aug. 29, 2016, 41 pages.
Non-Final Office Action mailed Oct. 6, 2022 in U.S. Appl. No. 16/927,860, 14 pages.
Non-Final Office Action mailed Sep. 19, 2019 in U.S. Appl. No. 15/122,394 for Chevillet et al., filed Aug. 29, 2016, 31 pages.
Notice of Allowance mailed Aug. 22, 2023 in U.S. Appl. No. 16/927,860, 8 pages.
Ozkumur, E. et al., "Inertial Focusing for Tumor Antigen—Dependent and—Independent Sorting of Rare Circulating Tumor", Sci Transl Med . Apr. 3, 2013; 5(179): 179ra47. doi:10.1126/scitranslmed.3005616. http://www.ncbi.nlm.nih.gov/pubmed/23552373.
Pinheiro, LB et al., "Evaluation of a droplet digital polymerase chain reaction format for DNA copy number quantification", (Translated from eng) Anal Chem 84(2):1003-1011, 2012.
Rago, C. et al., "Serial assessment of human tumor burdens in mice by the analysis of circulating DNA", (Translated from eng) Cancer Res 67(19):9364-9370, 2007.
Ren, XL et al., "Extracorporeal ablation of uterine fibroids with high-intensity focused ultrasound: imaging and histopathologic evaluation", Translated from eng) J Ultrasound Med 26(2):201-212, 2007.
Roobol, MJ et al., "The value of different screening tests in predicting prostate biopsy outcome in screening for prostate cancer data from a multicenter study (ERSPC)", (Translated from eng) Prostate 67(4):439-446, 2007.
Roychowdhury, S. et al., "Advancing Precision Medicine for Prostate Cancer Through Genomics", (Translated from Eng) J Clin Oncol, 2013.

(56) References Cited

OTHER PUBLICATIONS

Roychowdhury, S. et al., "Personalized oncology through integrative high-throughput sequencing: a pilot study", (Translated from eng) Sci Transl Med 3(111):111ra121, 2011.
Saad, A. et al., "Acute periprostatic haematoma following a transrectal ultrasound-guided needle biopsy of the prostate", (Translated from eng) Prostate Cancer Prostatic Dis 5(1):63-64, 2002.
Sacher, A. et al., "Prospective Validation of Rapid Plasma Genotyping for the Detection of EGFR and KRAS Mutations in", JAMA Oncol. Published online Apr. 7, 2016. doi:10.1001/jamaoncol.2016.0173.
Sawyers, CL , "The cancer biomarker problem", (Translated from eng) Nature 452(7187):548-552, 2008.
Stefani, G. et al., "Small non-coding RNAs in animal development", (Translated from eng) Nat Rev Mol Cell Biol 9(3):219-230, 2008.
Stroun, M. et al., "The origin and mechanism of circulating DNA", (Translated from eng) Ann N Y Acad Sci 906:161-168, 2000.
Sullivan, L. et al., "Canadian experience with high intensity focused ultrasound for the treatment of BPH", (Translated from Eng) Can J Urol 6(3):799-805, 1999.
Sullivan, Laurie , "Liquid Biopsies for Cancer Screening: an Emerging Sector of the POC Blood Testing Market", BCC Research. Jun. 15, 2015 http://www.bccresearch.com/lifesciences/index/liquid-biopsies.
Terry, M. , "Illumina (ILMN) Raises $100 Million with Amazon (AMZN)'s Bezos, Bill Gates and Others to Launch Pan-Cancer Test", Jan. 11, 2016. http://www.biospace.com/News/illumina-raises-100-million-with-amazons-bezos/405100.
The Promise of Liquid Biopsy Technology. Utilizing Investigational Technologies in Oncology Trials. 2016 Novella Clinical.
Thompson, IM et al., "Finasteride improves the sensitivity of digital rectal examination for prostate cancer detection", (Translated from eng) J Urol 177(5):1749-1752, 2007.
Thompson, IM et al., "Prevalence of prostate cancer among men with a prostate-specific antigen level < or =4.0 ng per milliliter", (Translated from eng) N Engl J Med 350(22):2239-2246, 2004.
Tie, J. et al., "Circulating tumor DNA analysis detects minimal residual disease and predicts recurrence in patients with stage II", Science Translational Medicine Jul. 6, 2016: vol. 8, Issue 346, pp. 346ra92. DOI: 10.1126/scitranslmed.aaf6219.
Tu, J. et al., "Intravascular inertial cavitation activity detection and quantification in vivo with Optison", (Translated from eng) Ultrasound Med Biol 32(10):1601-1609, 2006.
Vlaisavljevich, E. et al., "Effects of tissue mechanical properties on susceptibility to histotripsy-induced tissue damage.", Phys. Med. Bio. Jan. 2014., 20;59(2):253-70.
Wake, N. et al., "Chromosomal changes associated with progression of the Dunning R-3327 rat prostatic adenocarcinoma system", (Translated from eng) Cancer Res 42(10):4131-4142, 1982.
Wang, YN et al., "Histological and biochemical analysis of mechanical and thermal bioeffects in boiling histotripsy lesions induced by high intensity focused ultrasound", (Translated from eng) Ultrasound Med Biol 39(3):424-438, 2013.
Winslow, R. , "Genomic Health Plans Line of Liquid-Biopsy Tests for Cancer", Wall Street Journal. Jan. 11, 2015. http://www.wsj.com/articles/genomic-health-plans-line-of-liquid-biopsy-tests-for-cancer-1421023689.
Wolters, T. et al., "False-negative prostate needle biopsies: frequency, histopathologic features, and follow-up", (Translated from eng) Am J Surg Pathol 34(1):35-43, 2010.
Yuen, JS et al., "Clinical, biochemical and pathological features of initial and repeat transrectal ultrasonography prostate biopsy positive patients", (Translated from eng) Int J Urol 11(4):225-231, 2004.
Zhou, Y. et al., "Targeted long-term venous occlusion using pulsed high-intensity focused ultrasound combined with a pro-inflammatory agent", (Translated from eng) Ultrasound Med Biol 37(10):1653-1658, 2011.
Zill, O. et al., "Somatic genomic landscape of over 15,000 patients with advanced-stage cancer from clinical next-generation sequencing analysis of circulating tumor DNA", 2016 ASCO Annual Meeting. Abstract No. LBA11501. J Clin Oncol 34, 2016, http://meetinglibrary.asco.org/content/171265-176.

* cited by examiner

SYSTEMS AND METHODS FOR EVALUATING TISSUE OF A SUBJECT

CROSS-REFERENCE TO RELATED APPLICATION(S)

The present application is a continuation of U.S. patent application Ser. No. 16/936,095, titled "SYSTEMS AND METHODS FOR EVALUATING TISSUE OF A SUBJECT," filed Jul. 22, 2020, which is a continuation of U.S. patent application Ser. No. 15/122,394, titled "HIGH INTENSITY FOCUSED ULTRASOUND AND METHODS OF PERFORMING NON-INVASIVE BIOPSIES USING SAME," filed Aug. 29, 2016, which is a National Phase of International Patent Application No. PCT/US2015/024144, titled "HIGH INTENSITY FOCUSED ULTRASOUND AND METHODS OF PERFORMING NON-INVASIVE BIOPSIES USING SAME," filed Apr. 2, 2015, which claims priority to U.S. Provisional Patent Application No. 62/072,915, titled "SIMULATED RELEASE OF BIOMARKERS BY HIGH INTENSITY FOCUSED ULTRASOUND (HIFU); A MINIMALLY INVASIVE LIQUID BIOPSY," filed Oct. 30, 2014, and U.S. Provisional Patent Application No. 61/974,317, titled "SIMULATED RELEASE OF BIOMARKERS BY HIGH INTENSITY FOCUSED ULTRASOUND (HIFU); A MINIMALLY INVASIVE LIQUID BIOPSY," filed Apr. 2, 2014, the disclosures of which are hereby incorporated by reference in their entireties.

STATEMENT REGARDING FEDERALLY SPONSORED RESEARCH OR DEVELOPMENT

This invention was made with government support under R01 DK085714, K01 EB015745, and P50 CA097186, awarded by the National Institutes of Health, Transformative R01 Grant no. DK-085714, awarded by the National Institutes of Health. The government has certain rights in the invention.

SEQUENCE LISTING

This application contains an ST.26 compliant Sequence Listing, which is submitted concurrently in xml format via EFS-Web or Patent Center and is hereby incorporated by reference in its entirety. The .xml copy, created on Oct. 3, 2023 is named SequenceListing.xml and is 6.2 KB in size.

TECHNICAL FIELD

The present disclosure relates to systems and methods for selectively inducing release of a marker from a tissue mass of a subject using high intensity focused ultrasound (HIFU) energy.

BACKGROUND

The clinical evaluation of tissue masses (e.g., nodules, solid tumors, fibroids, cysts, etc.) typically includes performing a needle biopsy, which can provide diagnostic (benign vs. cancer) and molecular information (targetable mutations, drug resistance, etc). This procedure has several diagnostic limitations, most notably, the potential to miss the mutations only millimeters away. In response to these limitations, the concept of "liquid biopsy" has emerged in recent years: the detection of nucleic acid cancer biomarkers, such as tumor-derived microRNAs (miRNAs) and circulating tumor DNA (ctDNA). These biomarkers have shown high diagnostic value and could guide the selection of appropriate targeted therapies. However, the abundance of these biomarker classes in the circulation is often too low to be detectable—even with the most sensitive techniques—because of their low levels of release from the tumor.

Presently, the standard prostate biopsy strategy for diagnosing prostate cancer (PCA) utilizes an invasive transrectal procedure to obtain 12 needle-core specimens randomly sampled from the prostate. This approach has several diagnostic limitations and is associated with a significant and increasing number of infectious complications attributable to its invasive transrectal technique. A need exists for methods of performing biopsies that reduce or eliminate such complications.

P≤0.01, *P≤0.001, p-values calculated against mock treated, Dunns Multiple Comparison post-test.

Figure 7A:
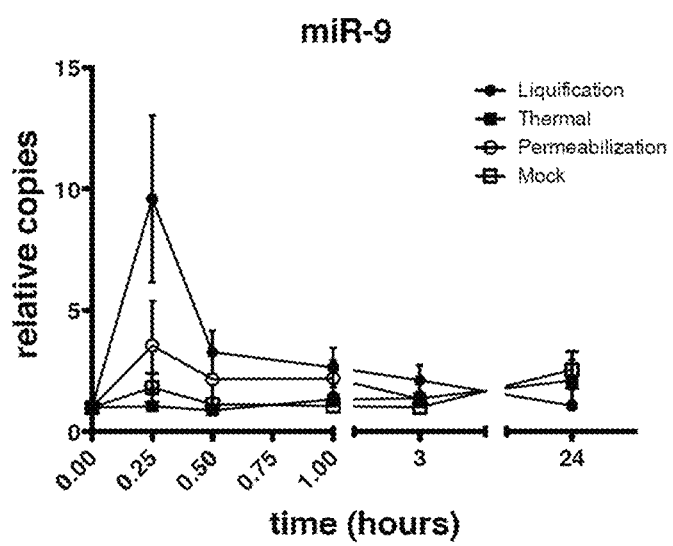
FIG. 7A shows the amount of miR-9 biomarker in blood samples obtained over time from tumor-implanted rats treated with liquification HIFU, thermal HIFU, permeabilization (histotripsy) HIFU, or mock treatment. *$P \leq 0.05$, $P \leq 0.01$, *$P \leq 0.001$, p-values calculated against mock treated, Dunns Multiple Comparison post-test.
Figure 7B:
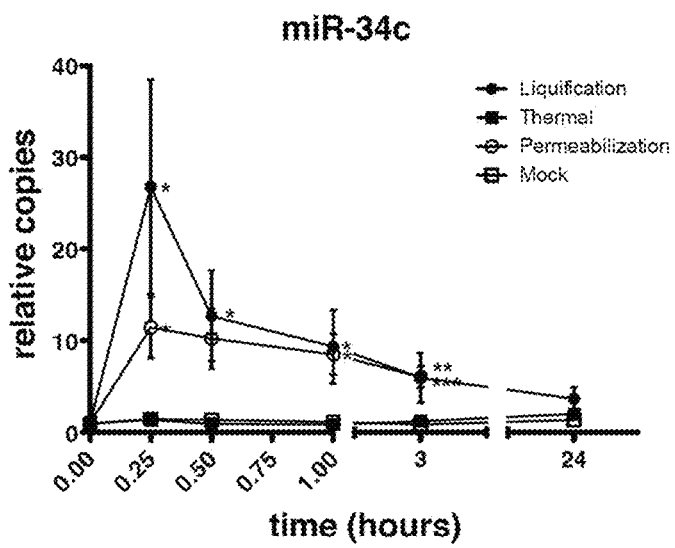
FIG. 7B shows the amount of miR-34c biomarker in blood samples obtained over time from tumor-implanted rats treated with liquification HIFU, thermal HIFU, permeabilization (histotripsy) HIFU, or mock treatment. *$P \leq 0.05$, $P \leq 0.01$, *$P \leq 0.001$, p-values calculated against mock treated, Dunns Multiple Comparison post-test.
Figure 7C:
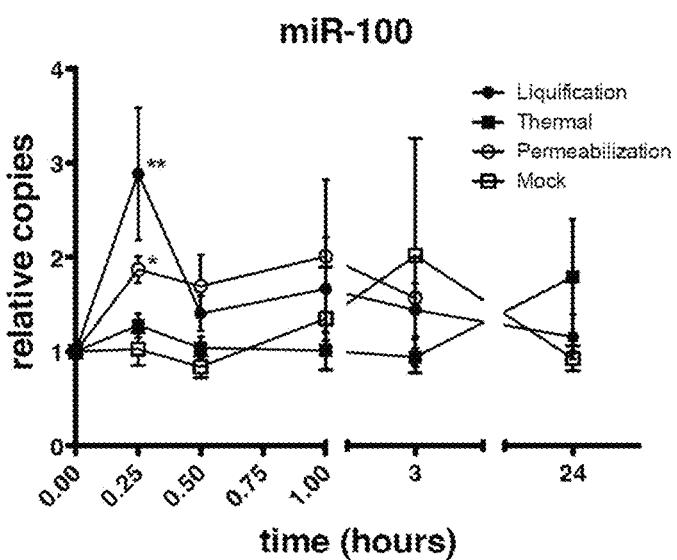
FIG. 7C shows the amount of miR-100 biomarker in blood samples obtained over time from tumor-implanted rats treated with liquification HIFU, thermal HIFU, permeabilization (histotripsy) HIFU, or mock treatment. *$P \leq 0.05$.
Figure 7D:
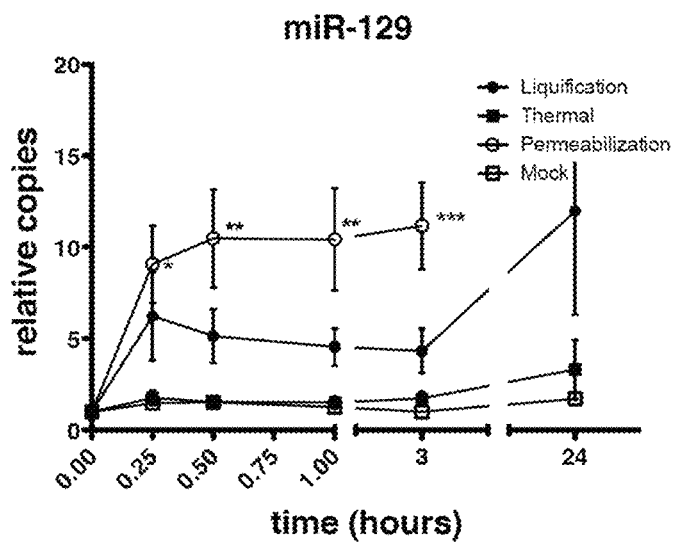

FIG. 7D shows the amount of miR-129 biomarker in blood samples obtained over time from tumor-implanted rats treated with liquification HIFU, thermal HIFU, permeabilization (histotripsy) HIFU, or mock treatment. *P≤0.05, P≤0.01, *P≤0.001, p-values calculated against mock treated, Dunns Multiple Comparison post-test.

Figure 7E:
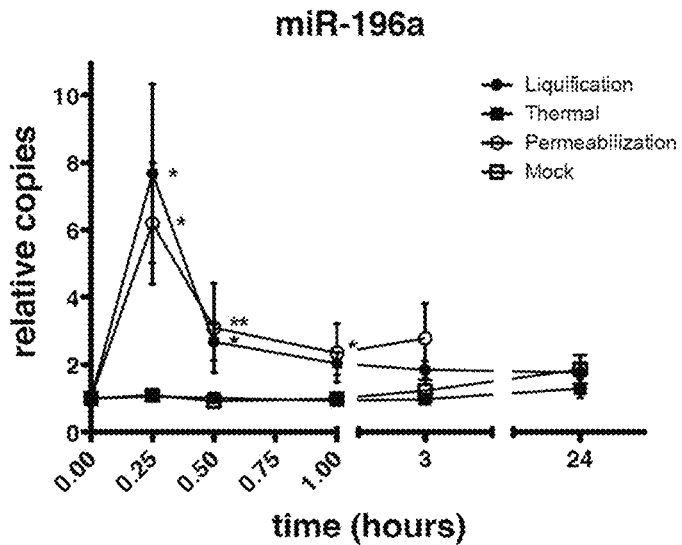

FIG. 7E shows the amount of miR-196a biomarker in blood samples obtained over time from tumor-implanted rats treated with liquification HIFU, thermal HIFU, permeabilization (histotripsy) HIFU, or mock treatment. *P≤0.05, P≤0.01, *P≤0.001, p-values calculated against mock treated, Dunns Multiple Comparison post-test.

Figure 7F:
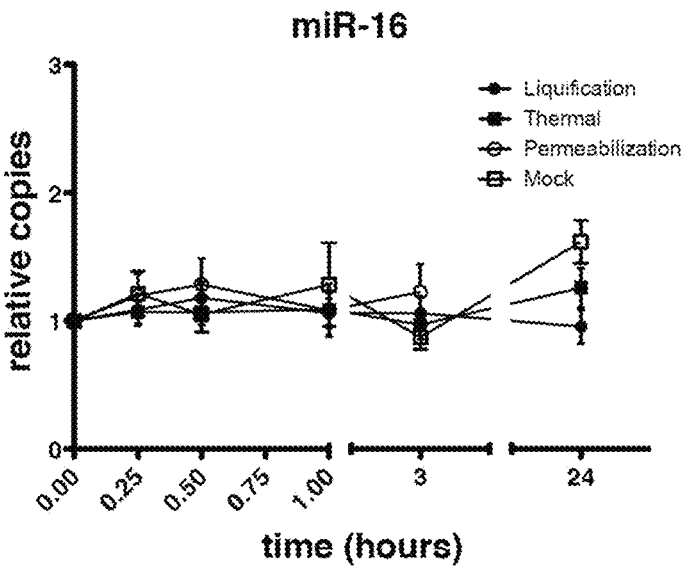

FIG. 7F shows the amount of miR-16 biomarker in blood samples obtained over time from tumor-implanted rats treated with liquification HIFU, thermal HIFU, permeabilization (histotripsy) HIFU, or mock treatment. *P≤0.05, P≤0.01, *P≤0.001, p-values calculated against mock treated, Dunns Multiple Comparison post-test.

Figure 8A:
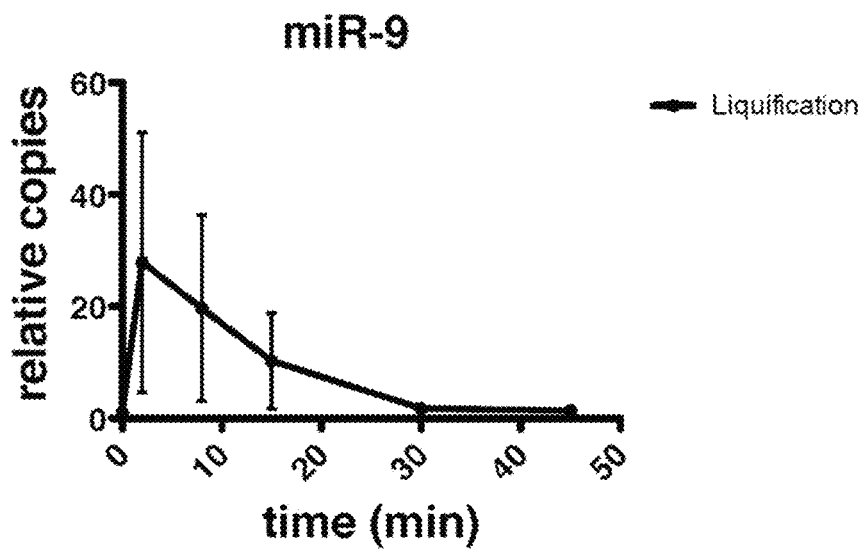

FIG. 8A displays relative copies of miR-9 biomarker in blood samples obtained more frequently over a shorter time course than those shown in FIG. 7A when the HIFU is a liquification regime. *P≤0.05, p-values calculated against pre-treatment miRNA abundance, Dunns Multiple Comparison post-test.

Figure 8B:
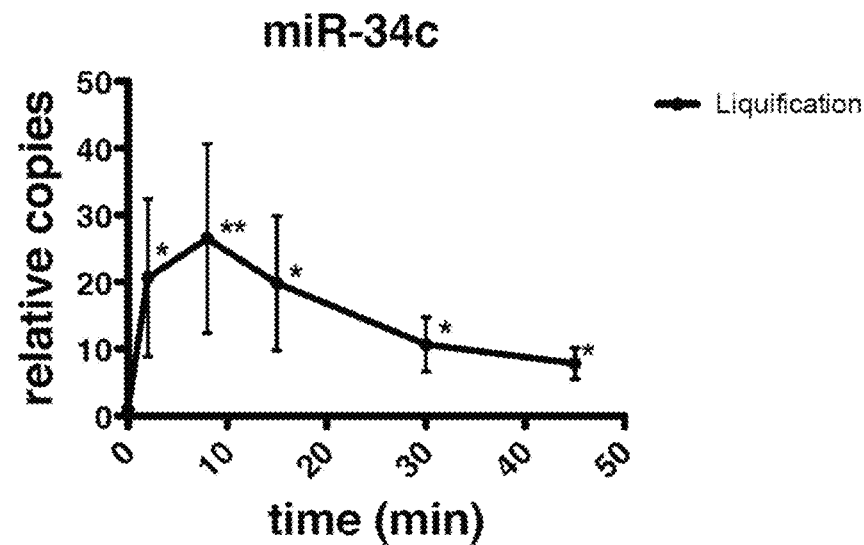

FIG. 8B displays relative copies of miR-34c biomarker in blood samples obtained more frequently over a shorter time course than those shown in FIG. 7B when the HIFU is a liquification regime. *P≤0.05, p-values calculated against pre-treatment miRNA abundance, Dunns Multiple Comparison post-test.

Figure 8C:
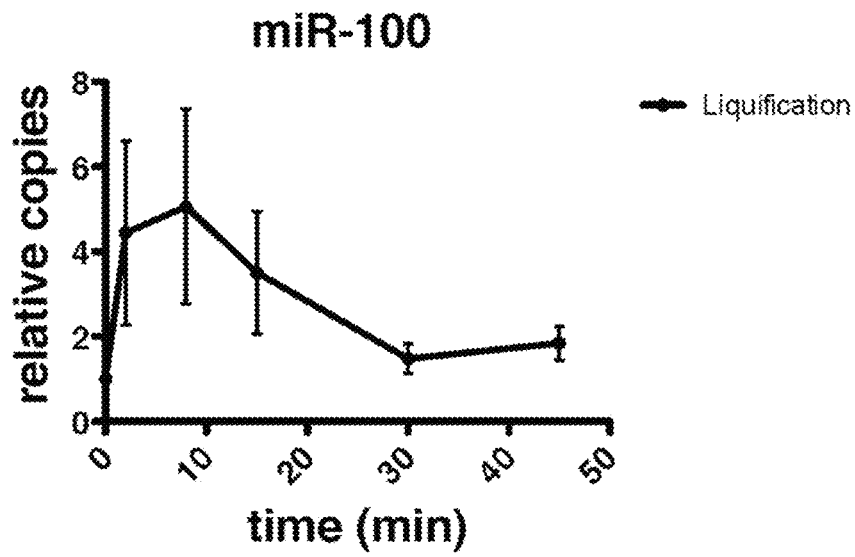

FIG. 8C displays relative copies of miR-100 biomarker in blood samples obtained more frequently over a shorter time course than those shown in FIG. 7C when the HIFU is a liquification regime. *P≤0.05, p-values calculated against pre-treatment miRNA abundance, Dunns Multiple Comparison post-test.

Figure 8D:
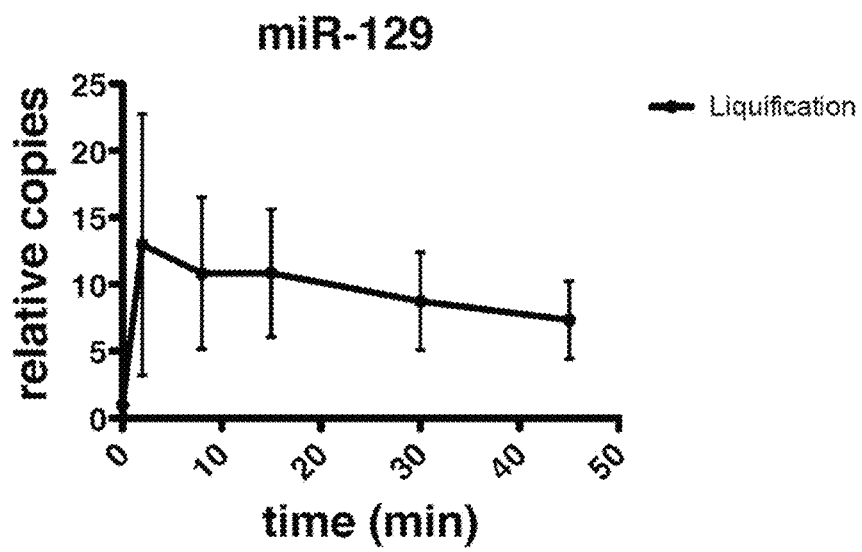

FIG. 8D displays relative copies of miR-129 biomarker in blood samples obtained more frequently over a shorter time course than those shown in FIG. 7D when the HIFU is a liquification regime. *P≤0.05, p-values calculated against pre-treatment miRNA abundance, Dunns Multiple Comparison post-test.

Figure 8E:
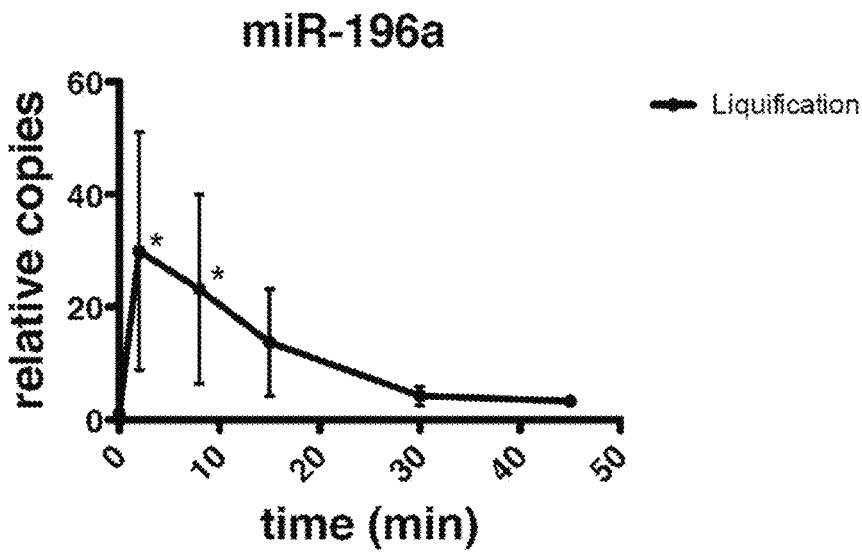

FIG. 8E displays relative copies of miR-196a biomarker in blood samples obtained more frequently over a shorter time course than those shown in FIG. 7E when the HIFU is a liquification regime. *P≤0.05, p-values calculated against pre-treatment miRNA abundance, Dunns Multiple Comparison post-test.

Figure 8F:
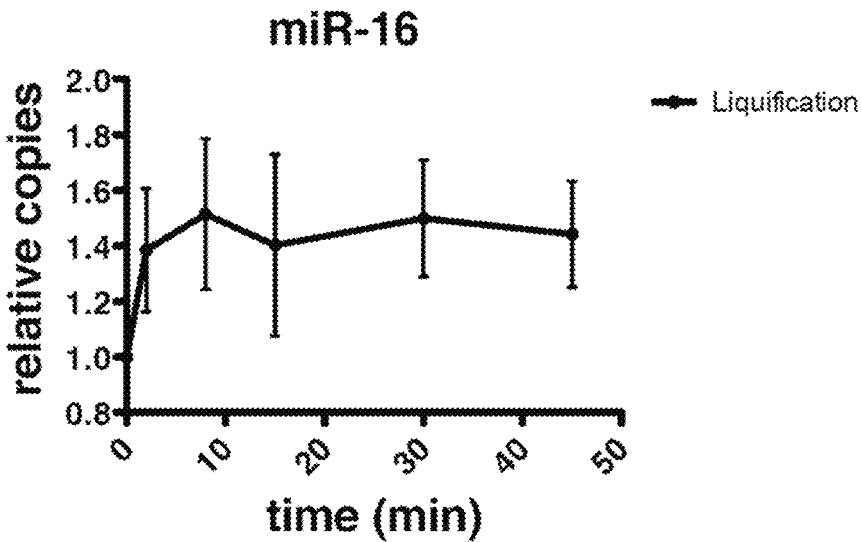

FIG. 8F displays relative copies of miR-16 biomarker in blood samples obtained more frequently over a shorter time course than those shown in FIG. 7F when the HIFU is a liquification regime. *P≤0.05, p-values calculated against pre-treatment miRNA abundance, Dunns Multiple Comparison post-test.

DETAILED DESCRIPTION

The present technology is directed toward systems and methods for selectively inducing release of a marker from a tissue mass. In several embodiments, for example, an ultrasound source can pulse HIFU energy toward a tissue mass or suspected tissue mass that includes one or more markers (e.g., a biomarker such as an miRNA), generally referred to herein as a "liquid molecular biopsy" technique. The pulsed HIFU waves can induce release of at least a portion of one or more markers into a fluid of a subject (e.g., the subject's blood stream), which can then be detected by conventional means. In some embodiments, the fluid is blood, such as a fluid and/or non-fluid fraction or derivative of blood like whole blood, cells, plasma, serum, microvesicles, and/or cryoprecipitate. In some embodiments, the HIFU energy is applied to the tissue mass or suspected tissue mass in a non-invasive or minimally invasive manner. The terms "tissue mass" and "suspected tissue mass" are used herein to describe various collections of cells which may be abnormal (including benign abnormal masses), such as nodules, cysts, tumors (e.g., prostate tumors). A single blood test can facilitate detection of the marker(s), and the resulting marker expression profile can be used to diagnose a condition (e.g., PCA) in a subject and provide critical individualized prognostic information for the subject. Systems and methods configured in accordance with embodiments of the present technology are expected to provide effective minimally invasive (e.g., non-invasive) diagnosis and/or treatment of tissue masses, and facilitate better informed, potentially personalized treatment related decisions while reducing risks commonly associated with conventional methods such as needle biopsy.

In some embodiments, a method of diagnosing a disease or an increased risk of a disease in a subject according to the present technology comprises applying high intensity focused ultrasound (HIFU) energy to a target mass of the subject to cause release of a marker from the mass; and thereafter determining a concentration of the marker in a fluid of the subject.

In other embodiments, a method of characterizing two or more masses in a human or non-human animal subject (collectively, the "subject") according to the present technology comprises optionally determining a baseline concentration of a first marker and/or a second marker in fluid of the subject; applying a first high intensity focused ultrasound (HIFU) energy to a first mass of the subject to cause release of a first marker from the mass; thereafter determining a concentration of the first marker in a first fluid sample of the subject; after a period of time, for example a period of time sufficient for the concentration of the first marker in the blood to return to or near a pre-HIFU baseline level, applying a second HIFU energy to a second mass of the subject to cause release of a second marker from the mass; thereafter determining a concentration of the second marker in a second fluid sample of the subject; and characterizing the first and second masses based, at least in part, on the concentrations of the first and second markers in the first and second fluid samples, respectively. In some embodiments, the first marker comprises a plurality of markers related to the first mass, and/or the second marker comprises a plurality of markers related to the second mass (e.g., multiplex biomarkers).

In other embodiments, a method of treating a target tissue mass in a human or non-human animal subject (collectively, the "subject") according to the present technology comprises optionally determining a baseline concentration of a biomarker in a fluid sample of the subject; performing a procedure on the target tissue mass of the patient; applying high intensity focused ultrasound (HIFU) energy to the target tissue mass; determining a concentration of the biomarker in a fluid sample of the subject after applying HIFU energy to the target tissue mass; and repeating the performing, applying, and determining until a concentration of the biomarker in the fluid sample falls below a threshold value.

In still other embodiments, a method of treating two or more tissue masses in a human or non-human animal subject (collectively, the "subject") according to the present technology comprises (a) optionally determining a baseline concentration of a first marker and/or second marker in fluid of the subject; (b) performing a first procedure on a first tissue mass of the subject; (c) applying high intensity focused ultrasound (HIFU) energy to the first tissue mass to cause a first marker to release from the first tissue mass; (d) thereafter, determining a concentration of the first marker in a first fluid sample of the subject; (e) after a first period of time, performing a second procedure on a second tissue mass of the subject; (f) applying HIFU energy to the second tissue mass to cause a second marker to release from the second tissue mass; (g) thereafter, determining a concentration of the second marker in a second fluid sample of the subject; and (h) after a second period of time, repeating: (1) steps (b) to (d) if the concentration of the first marker exceeds a first threshold value; (2) steps (e) to (g) if the concentration of the second marker exceeds a second threshold value; or (3) steps (b) to (g) if the concentration of the first marker exceeds the first threshold value and the concentration of the second marker exceeds the second threshold value.

In some embodiments, a method of inducing release of a marker from target tissue of a human or non-human animal subject according to the present technology comprises non-invasively applying high intensity focused ultrasound (HIFU) energy to the target tissue.

Certain specific details are set forth in the following description and in FIGS. 1-8F to provide a thorough understanding of various embodiments of the technology. For example, several embodiments of HIFU treatments that induce release of marker(s) from a tissue mass or suspected tissue mass are described in detail below. The present technology, however, may be used in conjunction with other therapy, such as a surgical procedure, immunotherapy (e.g., antitumor immunotherapy), ablation therapy (e.g., RF, cryotherapy, microwave therapy, laser therapy), radiation therapy, chemotherapy, brachytherapy, drug therapy (e.g., targeted drug therapy, chemotherapy, and/or non-chemotherapy), and the like. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-8F.

For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function. Further, the headings provided herein are for convenience only.

For ease of reference, throughout this disclosure systems and methods of treatment may refer to "a mass" or "a tissue mass." Unless the context clearly dictates otherwise, these terms may refer to a collection of cells (e.g., a tissue or a portion of a tissue), a region of one or more organs, a sarcoma, a tumor, a nodule, a cyst, or a combination thereof.

Figure 1:
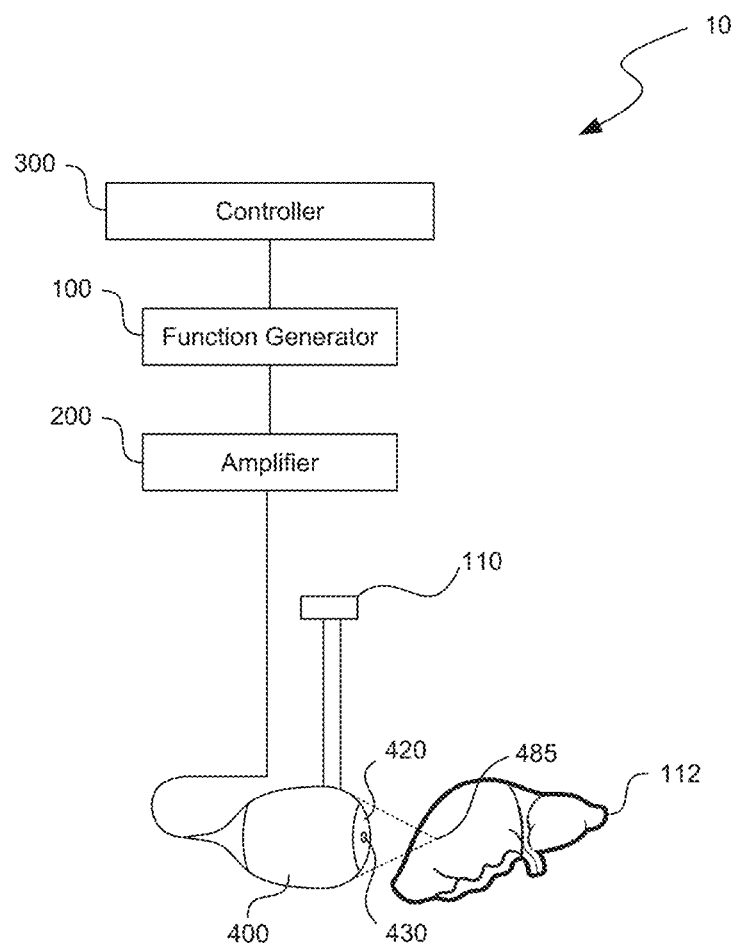
FIG. 1 is a partially schematic view of a liquid biopsy HIFU system configured to apply HIFU energy to a target tissue mass or an abscess of a patient or subject in accordance with an embodiment of the present technology.

Selected Embodiments of HIFU Systems for Performing Non-Invasive Biopsies and Associated Methods FIG. 1 is a partially schematic view of a liquid biopsy HIFU system 10 ("system 10") configured in accordance with an embodiment of the present technology. The system 10 can include an ultrasound source 400 operably coupled to a function generator 100 and, optionally, an amplifier 200. The ultrasound source 400 can be an ultrasound transducer that emits high levels of ultrasound energy toward a focus 485. The focus 485 can be a point, plane, region, or volume at which the intensity of the ultrasound energy emitted by the ultrasound source 400 is the highest. For example, the ultrasound source 400 generally has a focal depth equal to the diameter of the ultrasound transducer. The function generator 100 and the amplifier 200 can drive the ultrasound source 400 to radiate HIFU waves that induce boiling bubbles or cavitation proximate to the focus 485 to mechanically disrupt (e.g., reversibly disrupt or damage) the tissue mass or suspected tissue mass. Alternatively, the function generator 100 and the amplifier 200 can drive the ultrasound source 400 to radiate HIFU waves that heat or cause mild hyperthermia or irreversible heat damage to the tissue mass or suspected tissue mass. Accordingly, the system 10 can implement a pulsing protocol in which ultrasound frequency, pulse repetition frequency, pulse length, duty cycle, pressure amplitude, and/or other parameters associated with the HIFU emissions can be adjusted to generate HIFU waves to mechanically disrupt tissue at and/or in proximity to the focus 485.

Figure 2:
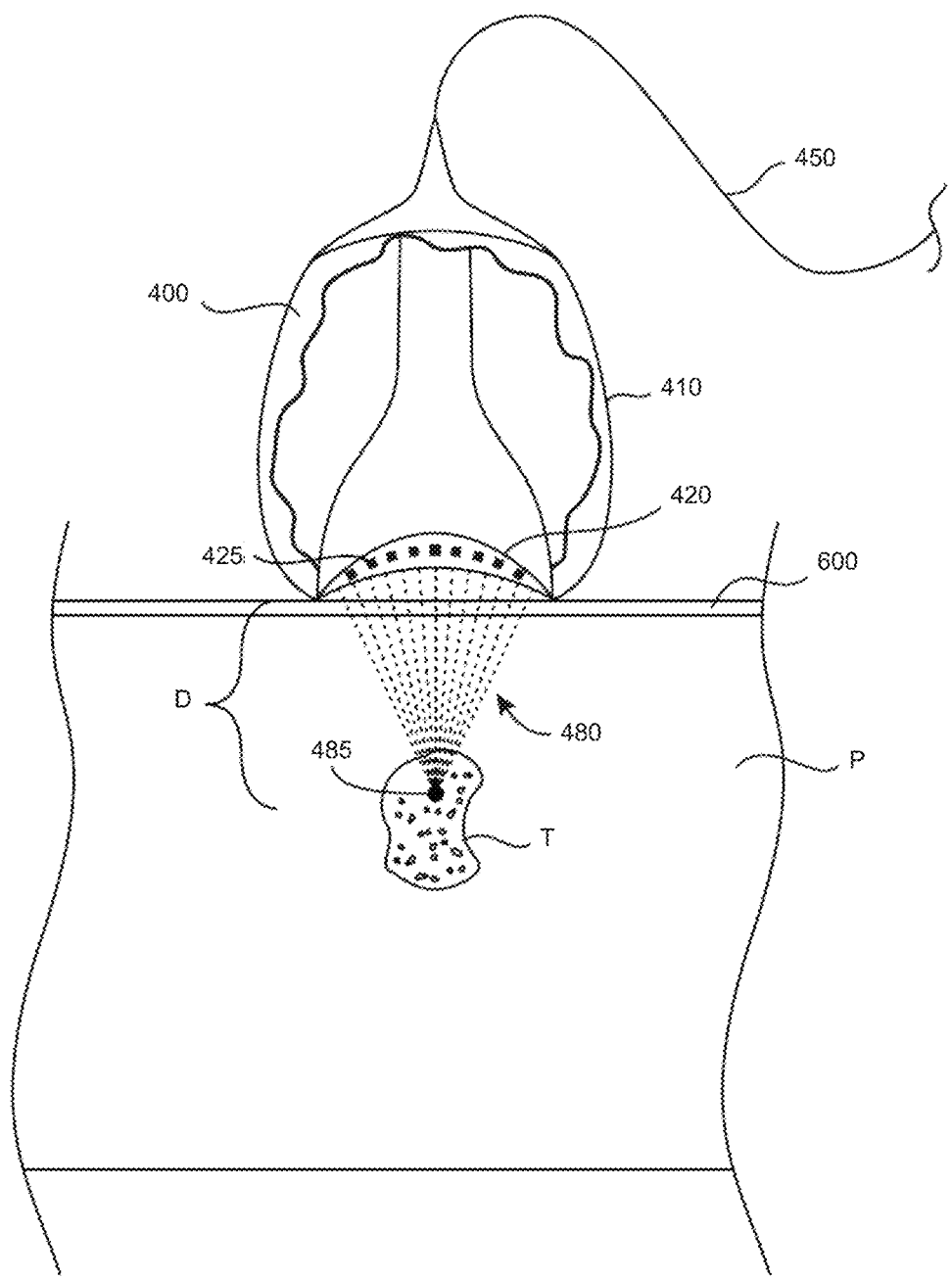
FIG. 2 is a partially schematic view of a method of applying HIFU energy to a target tissue mass or an abscess of a patient or subject using the system of FIG. 1.
Figure 3A:
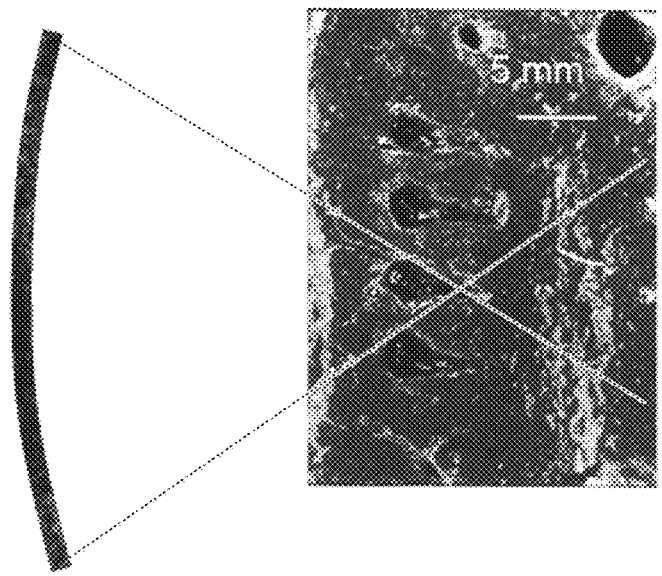
FIG. 3A shows repeatability of tissue cavities generated by ex vivo application of HIFU (10 ms pulse at 1 Hz for 50 seconds) to bovine liver, viewed in cross-section.
Figure 3B:
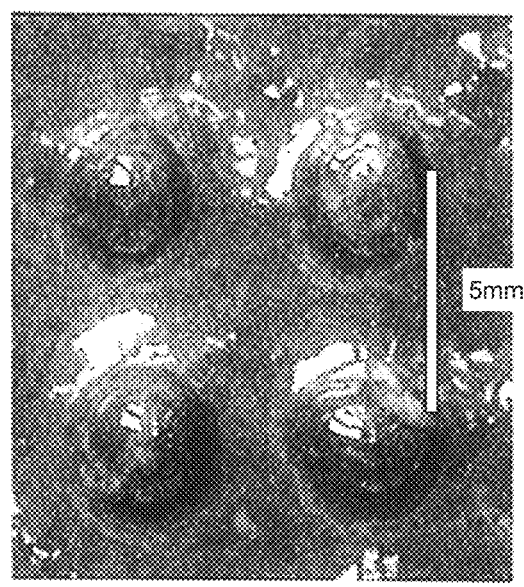
FIG. 3B shows repeatability of tissue cavities generated by ex vivo application of HIFU (10 ms pulse at 1 Hz for 50 seconds) to bovine liver, viewed in the focal plane.

The system 10 also includes an ultrasound source 400 configured for delivering the high-intensity ultrasound waveform to the target tissue mass or suspected tissue mass of the patient (see FIG. 2). In some embodiments, the system 10 further comprises a second transducer 430 for obtaining an ultrasound image of the tissue mass or suspected tissue mass. The second transducer 430 (when present) may comprise, for example, a diagnostic ultrasound transducer. Although the first ultrasound source 400 and second transducer 430 are shown in FIG. 1 within a single transducer housing (ultrasound wand), one of skill in the art will recognize that the second transducer 430 may also be housed in a separate transducer housing from the first ultrasound source 400 in other embodiments.

The system 10 may also comprise an optional controller 300 in operative communication with the function generator 100, the amplifier 200, and the ultrasound source 400. The system 10 may also include an optional display 500 in operative communication with the function generator 100, the amplifier 200, the ultrasound source 400, and the optional controller 300 (when present).

As noted previously, the system 10 is configured to deliver powerful, controlled ultrasound waves that are focused inside the patient's body to ablate the targeted tissue at the focus, without affecting or significantly affecting surrounding tissue or organ(s). In some embodiments, the HIFU waves are sent in short, infrequent but powerful bursts, causing mechanical disruption of tissue at the focus without any significant thermal effects (e.g., thermal damage). Without wishing to be bound by theory, it is believed that the mechanical disruption is achieved at least in part by the formation of small gas bubbles in the targeted tissue. These bubbles grow and collapse in response to the ultrasound wave, a phenomenon commonly referred to as cavitation. Depending on the pulsing protocol employed, the outcome can range from small holes in cell membranes and capillaries to complete liquefaction of a small region of tumor.

As shown in FIG. 1, the ultrasound source 400, the function generator 100, and/or other components of the system 10 can be coupled to a processor or controller 300 (shown schematically) that can be used to control the function and movement of various features of the system 10. In certain embodiments, the function generator 100 and the controller 300 can be integrated into a single device. The controller 300 can be processing device, such as a central processing unit (CPU) or computer. The controller 300 can include or be part of a device that includes a hardware controller that interprets the signals received from input devices (e.g., the ultrasound source 400, the function generator 100, user input devices, etc.) and communicates the information to the features of the system 10 using a communication protocol.

The controller 300 may be a single processing unit or multiple processing units in a device or distributed across multiple devices. The controller 300 may communicate with the hardware controller for devices, such as for a display that displays graphics and/or text (e.g., LCD display screens—not shown). The controller 300 can also be in communication with a memory that includes one or more hardware devices for volatile and non-volatile storage, and may include both read-only and writable memory. For example, a memory may comprise random access memory (RAM), read-only memory (ROM), writable non-volatile memory, such as flash memory, hard drives, floppy disks, CDs, DVDs, magnetic storage devices, tape drives, device buffers, and so forth. A memory is not a propagating electrical signal divorced from underlying hardware, and is thus non-transitory. In certain embodiments, the controller 108 can also be coupled to a communication device capable of communicating wirelessly or wire-based with a network node. The communication device may communicate with another device or a server through a network using, for example, TCP/IP protocols.

The controller 300 can execute automated control algorithms to initiate, terminate, and/or adjust operation of one or more features of the system 10 and/or receive control instructions from a user. The controller 300 can further be configured to provide feedback to a user based on the data received from the system 10 via an evaluation/feedback algorithm. This information can be provided to the users via a display (e.g., a monitor on a computer, tablet computer, or smart phone; not shown) communicatively coupled to the controller.

In various embodiments, the system 10 can further include a positioning device 110 coupled to the ultrasound source 400 to aid in positioning the focus 485 of the ultrasound source 400 at a desired target site in the tissue. For example, the positioning device 110 can include a three-axis computer-controlled positioning system. The positioning device 110 can also manipulate the ultrasound source 400 to move the focus 485 to different regions in the tissue to mechanically damage larger portions of the tissue 112. In other embodiments, the system 10 can include additional devices and/or some of the devices may be omitted from the system 10.

In operation, the ultrasound source 400 is positioned proximate to a volume of tissue 112 (e.g., an organ), and the focus 485 of the ultrasound source 400 is aligned with a target site within the tissue 112 using the positioning device 110. For example, the ultrasound source 400 can be positioned such that its focus 485 is a depth within an ex vivo or in vivo liver, kidney, heart, and/or other tissue mass and aligned with a tumor, cancerous tissue region, and/or other volume of tissue that a clinician would like to mechanically damage. HIFU energy can be delivered from the ultrasound source 400 to the target site in the tissue 112 in a sequence of pulses (e.g., coordinated by the function generator 100 and/or the controller 300) rather than continuous-wave HIFU exposures, which can reduce undesirable thermal effects on the surrounding tissue. Larger target sites can be treated by scanning the focus 485 of the ultrasound source 400 over the treatment region (e.g., using the positioning device 110) while pulsing HIFU energy toward the tissue 112.

In various embodiments, the system 10 can deliver a pulsing protocol to provide boiling histotripsy that mechanically fractionates the tissue. During boiling histotripsy, the ultrasound source 400 propagates millisecond-long bursts of non-linear HIFU waves toward the focal region 485 in the tissue 112, and the accumulation of the harmonic frequencies produces shock fronts proximate to the focal region 485. This results in rapid heating of tissue and boiling bubbles at the focal region 485 that liquefy and otherwise mechanically damages the tissue 112.

In certain embodiments, the function generator 100 can initiate a pulsing protocol to generate shock waves with peak positive amplitudes of about 5 MPa to about 100 MPa at the focus 485, about 15 MPa to about 90 MPa at the focus 485, about 25 MPa to about 80 MPa at the focus 485, about 35 MPa to about 70 MPA at the focus 485, or about 45 MPa to about 60 MPa at the focus 485, for example 5 MPa, about 10 MPa, about 15 MPa, about 20 MPa, about 25 MPa, about 30 MPa, about 35 MPa, about 40 MPa, about 45 MPa, about 50 MPa, about 55 MPa, about 60 MPa, about 65 MPa, about 70 MPa, about 75 MPa, about 80 MPa, about 85 MPa, about 90 MPa, about 95 MPa, or about 100 MPa at the focus 485. In other embodiments, the shock wave amplitudes may differ depending, at least in part, on the power driving the ultrasound source 400.

In certain embodiments, the function generator 100 can initiate a pulsing protocol to generate shock waves with peak negative pressures of about −3 MPa to about −25 MPa at the focus 485, about −5 MPa to about −20 MPa at the focus 485, or about −10 MPa to about −15 MPa at the focus 485, for example about −3 MPa, about −4 MPa, about −5 MPa, about −6 MPa, about −7 MPa, about −8 MPa, about −9 MPa, about −10 MPa, about −11 MPa, about −12 MPa, about −13 MPa, about −14 MPa, about −15 MPa, about −16 MPa, about −17 MPa, about −18 MPa, about −19 MPa, about −20 MPa, about −21 MPa, about −22 MPa, about −23 MPa, about −24 MPa, or about −25 MPa at the focus 485.

In certain embodiments, the function generator 100 can initiate a pulsing protocol to generate shock waves including a single frequency of ultrasound energy or more than one frequency of ultrasound energy. In some embodiments, for example, the ultrasound waveform comprises an ultrasound frequency of about 1 MHz to about 3 MHz at the focus 485, or about 1.5 MHz to about 2.5 MHz at the focus 485, for example about 1 MHz, about 1.1 MHz, about 1.2 MHz, about 1.3 MHz, about 1.4 MHz, about 1.5 MHz, about 1.6 MHz, about 1.7 MHz, about 1.8 MHz, about 1.9 MHz, about 2 MHz, about 2.1 MHz, about 2.2 MHz, about 2.3 MHz, about 2.4 MHz, about 2.5 MHz, about 2.6 MHz, about 2.7 MHz, about 2.8 MHz, about 2.9 MHz, or about 3 MHz at the focus 485. In some embodiments, the frequency is selected to provide a focal area that is smaller than the size of the tissue mass or suspected tissue mass and/or to provide an attenuation (e.g., depth) sufficient to contact the tissue mass or suspected tissue mass with the ultrasound energy.

The function generator 100 is also configured to provide a specific form (e.g., shape, pulse pattern, etc.) to the ultrasound energy. In some embodiments, for example, the function generator 100 is configured to provide an ultrasound energy waveform comprising periodic pulse sequences, non-periodic pulse sequences, or a combination thereof. For example, in some embodiments the function generator 100 is configured to provide an ultrasound energy waveform comprising a sinusoidal waveform. In other embodiments, the function generator 100 is configured to provide an ultrasound energy waveform comprising a square waveform. In still further embodiments, the function generator 100 is configured to provide an ultrasound energy waveform comprising a peaked waveform. In yet other embodiments, the function generator 100 may be configured to provide an ultrasound energy waveform comprising a combination of any of the foregoing.

In certain embodiments, the function generator 100 can initiate a pulsing protocol to generate shock waves with a pulse-average intensity of about 10 kW/cm$^2$ to about 60 kW/cm$^2$ at the focus 485, about 20 kW/cm$^2$ to about 50 kW/cm$^2$ at the focus 485, or about 30 kW/cm$^2$ to about 40 kW/cm$^2$ at the focus 485, for example about 10 kW/cm$^2$, about 11 kW/cm$^2$, about 12 kW/cm$^2$, about 13 kW/cm$^2$, about 14 kW/cm$^2$, about 15 kW/cm$^2$, about 16 kW/cm$^2$, about 17 kW/cm$^2$, about 18 kW/cm$^2$, about 19 kW/cm$^2$, about 20 kW/cm$^2$, about 21 kW/cm$^2$, about 22 kW/cm$^2$, about 23 kW/cm$^2$, about 24 kW/cm$^2$, about 25 kW/cm$^2$, about 26 kW/cm$^2$, about 27 kW/cm$^2$, about 28 kW/cm$^2$, about 29 kW/cm$^2$, about 30 kW/cm$^2$, about 31 kW/cm$^2$, about 32 kW/cm$^2$, about 33 kW/cm$^2$, about 34 kW/cm$^2$, about 35 kW/cm$^2$, about 36 kW/cm$^2$, about 37 kW/cm$^2$, about 38 kW/cm$^2$, about 39 kW/cm$^2$, about 40 kW/cm$^2$, about 41 kW/cm$^2$, about 42 kW/cm$^2$, about 43 kW/cm$^2$, about 44 kW/cm$^2$, about 45 kW/cm$^2$, about 46 kW/cm$^2$, about 47 kW/cm$^2$, about 48 kW/cm$^2$, about 49 kW/cm$^2$, about 50 kW/cm$^2$, about 51 kW/cm$^2$, about 52 kW/cm$^2$, about 53 kW/cm$^2$, about 54 kW/cm$^2$, about 55 kW/cm$^2$, about 56 kW/cm$^2$, about 57 kW/cm$^2$, about 58 kW/cm$^2$, about 59 kW/cm$^2$, or about 60 kW/cm$^2$ at the focus 485.

In certain embodiments, the function generator 100 can initiate a pulsing protocol to generate shock waves with a pulse duration of about 1 microsecond (μs) to about 100 miliseconds milliseconds (ms), about 10 μs to about 10 ms, or about 100 μs to about 1 ms, for example about 1 μs, about 5 μs, about 10 μs, about 15 μs, about 20 μs, about 25 μs, about 30 μs, about 35 μs, about 40 μs, about 45 μs, about 50 μs, about 55 μs, about 60 μs, about 65 μs, about 70 μs, about 75 μs, about 80 μs, about 85 μs, about 90 μs, about 95 μs, about 100 μs, about 125 μs, about 150 μs, about 175 μs, about 200 μs, about 225 μs, about 250 μs, about 275 μs, about 300 μs, about 325 μs, about 350 μs, about 375 μs, about 400 μs, about 425 μs, about 450 μs, about 475 μs, about 500 μs, about 525 μs, about 550 μs, about 575 μs, about 600 μs, about 625 μs, about 650 μs, about 675 μs, about 700 μs, about 725 μs, about 750 μs, about 775 μs, about 800 μs, about 825 μs, about 850 μs, about 875 μs, about 900 μs, about 925 μs, about 950 μs, about 975 μs, about 1 ms, about 5 ms, about 10 ms, about 15 ms, about 20 ms, about 25 ms, about 30 ms, about 35 ms, about 40 ms, about 45 ms, about 50 ms, about 55 ms, about 60 ms, about 65 ms, about 70 ms, about 75 ms, about 80 ms, about 85 ms, about 90 ms, about 95 ms, or about 100 ms.

In certain embodiments, the function generator 100 can initiate a pulsing protocol to generate shock waves with a duty cycle of about 0.1% to about 5%, about 0.5% to about 3%, or about 1% to about 2%, for example about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%.

The amplifier 200 may also be configured to output an amplified ultrasound energy waveform that is nonlinearly distorted at the focus 485. Further, the amplifier 200 may be configured to output an amplified ultrasound energy waveform having more than one peak pressure.

In certain embodiments, the function generator 100 can initiate a pulsing protocol to generate shock waves with a peak negative pressure of about −3 MPa to about −25 MPa, a peak positive pressure of about 5 MPa to about 100 MPa, a frequency of about 1 MHz to about 3 MHz, and a pulse duration of about 1 μs to about 100 ms. In some embodiments, the waveform further has a duty cycle of about 0.1% to about 5%. In some embodiments, the waveform further is nonlinearly distorted at the focal point.

The ultrasound source 400 is operatively coupled with one or more components of the system 10 and is configured to administer (e.g., apply, deliver, etc.) the amplified ultrasound energy waveform to a tissue mass or a suspected tissue mass. In some embodiments, such as that shown in FIG. 2, the ultrasound source 400 includes a transducer head 420 including one or more transducer elements 425 and configured to focus the amplified ultrasound energy waveform within a tissue mass or within a suspected tissue mass of a subject. In some embodiments, the ultrasound source 400 may additionally include a second transducer head 430 for obtaining an image of the tissue mass or suspected tissue mass for monitoring application of the amplified ultrasound energy waveform to the tissue mass or suspected tissue mass. In other embodiments, the second transducer head 430 is housed in a second, separate transducer. In other embodiments, the ultrasound source 400 includes a single transducer head 420 for focusing the amplified ultrasound energy waveform (e.g., HIFU) and for obtaining an image of the tissue mass or suspected tissue mass for monitoring application of the amplified ultrasound energy waveform to the tissue mass or suspected tissue mass. In such embodiments, the transducer head 420 may include a linear array of transducer elements 425 which may provide focused amplified ultrasound energy (e.g., HIFU) at a desired depth by generating multiple pulses of the energy from each transducer element 425, wherein the multiple pulses are separated in time (e.g., delayed) according to methods known to those in the art.

The transducer head 420 is arranged to provide the amplified ultrasound energy waveform with an adjustable focus. In some embodiments, for example, the transducer head 420 includes an array of transducer elements 425, each of which may be energized in a pattern sufficient to provide the amplified ultrasound energy waveform having a focus located at a preselected distance from the ultrasound source 400. FIG. 2, for example, is a partially schematic view of a method of applying HIFU energy to a tissue mass or suspected tissue mass T using the system 10. As shown in the embodiment of FIG. 2, the transducer head 420 has a generally concave shape, providing an array of transducer elements 425 in a generally concave pattern. The resulting amplified ultrasound energy waveform 480 provided by the ultrasound source 400 includes a focal point 485 located a predetermined focal distance D from the ultrasound source 400. The focal distance D may be selected to correspond to the location (e.g., depth) of a tissue mass or suspected tissue mass T, such that the focal point 485 is located within the tissue mass or suspected tissue mass T of a patient P. One of skill in the art will recognize, however, that other arrangements of transducer elements 425 are possible. For example, linear arrays of transducer elements 425 or transducer elements 425 arranged in other suitable patterns may also be used. In addition, the focal distance D may be determined or adjusted by altering the phasing of the amplified ultrasound energy waveform provided to each of the transducer elements 425.

Referring to FIGS. 1 and 2 together, and as noted previously, the controller 300 is in operative communication with the function generator 100, the amplifier 200, and the ultrasound source 400. The controller 300 may be used, for example, to receive input from a clinician regarding the focal distance D required, the extent of amplification required by the amplifier 200, and/or the shape of the ultrasound energy waveform generated by the function generator 100. In some embodiments, the controller 300 is configured to receive data (e.g., imaging data) from a second transducer 430 and determine a focal distance D based on the data. The controller 300 may also be configured to automatically determine and/or automatically adjust the extent of amplification provided by the amplifier, the shape of the waveform provided by the function generator 100, and/or a pattern of energizing one or more transducer elements 425 as a function of imaging data showing the tissue mass or suspected tissue mass T to be treated (e.g., including a depth of the tissue mass or suspected tissue mass T below the surface of the patient P's skin.

In any of the embodiments disclosed herein, the system 10 may be configured to be portable. In such embodiments, the system 10 may further include a battery (not shown) for providing power to the system 10. In further embodiments, one or more of the components of the system 10 may be wirelessly coupled to the other components of the system 10. Additionally, the system 10 may include one or more additional features or the components may have a different arrangement relative to each other.

Methods of diagnosing and/or treating a tissue mass or suspected tissue mass T may include the use of the systems and/or components described herein (such as the system 10 described above with reference to FIGS. 1 and 2) or other suitable HIFU systems. In some embodiments, for example, the present technology provides a method of diagnosing and/or treating a tissue mass or suspected tissue mass associated with a subject by applying ultrasound energy to the tissue mass or suspected tissue mass sufficient to cause one or more biomarkers to be released from the target tissue, for example by stimulating, perturbing or disrupting (e.g., reversibly disrupting) at least a portion of the tissue mass or suspected tissue mass. The biomarker may be associated with a particular type of cancer.

In some embodiments, for example, the tissue mass or suspected tissue mass may be associated with prostate cancer. In such embodiments, the corresponding marker(s) (e.g., biomarker(s)) is also associated with prostate cancer. In some embodiments, the biomarker is hsa-miR-9-5p (SEQ ID NO:1). In some embodiments, the biomarker is hsa-miR-196a-5p (SEQ ID NO:2). In some embodiments, the biomarker is hsa-miR-34c-5p (SEQ ID NO:3). In some embodiments, the biomarker is hsa-miR-129-5p (SEQ ID NO:4). In some embodiments, the biomarker is hsa-miR-100-5p (SEQ ID NO:5). In some embodiments, the biomarker is hsa-miR-16-5p (SEQ ID NO:6). In some embodiments, the marker is a DNA, an RNA or a protein. In other embodiments, the biomarker is a known prostate cancer biomarker, such as prostate cancer antigen 3 (PCA3) RNA, a TMPRSS2-ERG fusion (e.g., DNA or RNA), a diagnostic androgen receptor (AR) DNA or RNA or protein, a phosphatase and tensin homolog (PTEN) (e.g., a PTEN RNA or DNA), TP53 (p53) RNA or DNA, a Kirsten rat sarcoma viral oncogene homolog (KRAS), an NKX3.1 DNA or RNA, a CDH1 (aka Ecad, E-cadherin) DNA or RNA or protein, an APC DNA or RNA, a BRAF DNA or RNA, an src DNA or RNA, an abl DNA or RNA, an raf DNA or RNA, an erbA DNA or RNA, or an myc DNA or RNA.

In other embodiments, the tissue mass or suspected tissue mass and corresponding marker (e.g., biomarker) may be associated with ovarian cancer. For example, in some embodiments, the biomarker is hsa-miR-9-5p (SEQ ID NO:1). In some embodiments, the biomarker is hsa-miR-196a-5p (SEQ ID NO:2). In some embodiments, the biomarker is hsa-miR-34c-5p (SEQ ID NO:3). In some embodiments, the biomarker is hsa-miR-129-5p (SEQ ID NO:4). In some embodiments, the biomarker is hsa-miR-100-5p (SEQ ID NO:5). In some embodiments, the biomarker is hsa-miR-16-5p (SEQ ID NO:6). In other embodiments, the biomarker is a known ovarian cancer biomarker, such as a TP53 (aka p53) RNA or DNA, BRCA1 or BRCA2 (DNA or RNA), an src DNA or RNA, a raf DNA or RNA, an erbA DNA or RNA, or a myc DNA or RNA.

In other embodiments, the tissue mass or suspected tissue mass and corresponding marker (e.g., biomarker) may be associated with breast cancer. For example, in some embodiments, the biomarker is hsa-miR-9-5p (SEQ ID NO:1). In some embodiments, the biomarker is hsa-miR-196a-5p (SEQ ID NO:2). In some embodiments, the biomarker is hsa-miR-34c-5p (SEQ ID NO:3). In some embodiments, the biomarker is hsa-miR-129-5p (SEQ ID NO:4). In some embodiments, the biomarker is hsa-miR-100-5p (SEQ ID NO:5). In some embodiments, the biomarker is hsa-miR-16-5p (SEQ ID NO:6). In other embodiments, the biomarker is a known breast cancer biomarker, such as a TP53 (aka p53) RNA or DNA, an APC DNA or RNA, a BRAF DNA or RNA, an src DNA or RNA, a raf DNA or RNA, an erbA DNA or RNA, a myc DNA or RNA, BRCA1 or BRCA2 (DNA or RNA), or an HER2/neu (DNA and RNA).

In still other embodiments, the tissue mass or suspected tissue mass and corresponding marker (e.g., biomarker) may be associated with renal cell carcinoma. In some embodiments, for example, the biomarker is hsa-miR-9-5p (SEQ ID NO:1). In some embodiments, the biomarker is hsa-miR-196a-5p (SEQ ID NO:2). In some embodiments, the biomarker is hsa-miR-34c-5p (SEQ ID NO:3). In some embodiments, the biomarker is hsa-miR-129-5p (SEQ ID NO:4). In some embodiments, the biomarker is hsa-miR-100-5p (SEQ ID NO:5). In some embodiments, the biomarker is hsa-miR-16-5p (SEQ ID NO:6). In other embodiments, the biomarker is a known renal cell carcinoma biomarker, such as a phosphatase and tensin homolog (PTEN) RNA or DNA, a von Hippel-Lindau syndrome (VHL) DNA or RNA, a TP53 (aka p53) RNA or DNA, an src DNA or RNA, a raf DNA or RNA, or an erbA DNA or RNA.

In further embodiments, the tissue mass or suspected tissue mass and corresponding marker (e.g., biomarker) may be associated with a uterine fibroid. For example, in some embodiments, the biomarker is hsa-miR-9-5p (SEQ ID NO:1). In some embodiments, the biomarker is hsa-miR-196a-5p (SEQ ID NO:2). In some embodiments, the biomarker is hsa-miR-34c-5p (SEQ ID NO:3). In some embodiments, the biomarker is hsa-miR-129-5p (SEQ ID NO:4). In some embodiments, the biomarker is hsa-miR-100-5p (SEQ ID NO:5). In some embodiments, the biomarker is hsa-miR-16-5p (SEQ ID NO:6). In other embodiments, the biomarker is a known uterine fibroid biomarker, such as gene mediator subcomplex 12 (MED12) DNA or RNA.

In some embodiments, methods according to the present technology can further include introducing an ultrasound contrast agent to the tissue mass or suspected tissue mass (e.g., by administering an antibody-microbubble conjugate or a peptide-microbubble conjugate to the subject, or by administering a systemic ultrasound contrast agent to the subject) before applying HIFU energy to the target tissue. Without wishing to be bound by theory, the ultrasound contrast agent is expected to enhance the effect of the applied ultrasound energy (e.g., HIFU), for example, by enabling an enhanced amount of a biomarker to be released from the tissue mass or suspected tissue mass.

When used in conjunction with a therapeutic protocol (e.g., anti-tumor therapies), the present technology is also expected to significantly enhance a clinician's ability to assess and monitor the effectiveness of treatment. For example, when using therapeutic techniques that often require more than one application of a therapy (e.g., radiation), the present technology enables a clinician to apply a first round of therapy to a tissue mass, assess the effectiveness of the therapy by applying an amplified ultrasound energy wave (e.g., HIFU) to the tissue mass and measuring an amount of a selected biomarker in a fluid sample (e.g., a blood sample, such as a fluid and/or non-fluid fraction or derivative of blood like whole blood, cells, plasma, serum, microvesicles, and/or cryoprecipitate) obtained from the subject, and determine (based on the amount of the biomarker in the fluid sample) whether additional round(s) of therapy are warranted. Because methods according to the current technology cause rapid release of the biomarker from the tissue mass (e.g., within 10 minutes or within 5 minutes), the tissue mass can be conveniently be-treated multiple times within a single procedure (e.g., single visit to a treatment clinic).

EXAMPLES

Example 1

HIFU was applied to prostate cancer tumors implanted under the skin of laboratory rats. Conventional ultrasound imaging was used or image guidance and targeting. Blood samples were collected immediately before and at periodic intervals after HIFU treatment (boiling histotripsy and cavitation regimes), and were tested for the presence of microRNAs ("miRNAs") that are associated with rat prostate cancer, shown in Table 1.

TABLE 1

Putative miRNA biomarker sequences.

| miRNA* | RNA sequence (human and rat) |
| --- | --- |
| miR-9-5p | UCUUUGGUUAUCUAGCUGUAUGA (SEQ ID NO: 1) |
| miR-196a-5p | UAGGUAGUUUCAUGUUGUUGGG (SEQ ID NO: 2) |
| miR-34c-5p | AGGCAGUGUAGUUAGCUGAUUGC (SEQ ID NO: 3) |
| miR-129-5p | CUUUUUGCGGUCUGGGCUUGC (SEQ ID NO: 4) |

TABLE 1-continued

Putative miRNA biomarker sequences.

| miRNA* | RNA sequence (human and rat) |
| --- | --- |
| miR-100-5p | AACCCGUAGAUCCGAACUUGUG (SEQ ID NO: 5) |
| miR-16-5p | UAGCAGCACGUAAAUAUUGGCG (SEQ ID NO: 6) |

*Equivalent miRNA species may be referred to herein with or without the "5p" suffix.

The levels of these miRNAs were elevated up to 30-fold within minutes after the ultrasound procedure, and then declined over the course of several hours. The effects on tissue were evaluated in the resected tumors, and only micron-sized areas of hemorrhage scattered through otherwise intact tissue were found when the HIFU was applied as a cavitation regime, suggesting damage to small capillaries. Liquefaction HIFU caused substantial disruption to the tissue in corollary experiments. These data provided the proof of principle for the technology disclosed herein directed to "ultrasound-aided liquid molecular biopsy".

Example 2

Objectives: The ability of ultrasound to stimulate the release of cancer-specific protein biomarkers into the circulation was recently reported, however, physical and biological mechanisms behind it are unclear. In addition, the protein biomarker in that study (carcinoembryonic antigen, CEA) is expressed on the cell surface, thus providing no proof of principal for releasing biomarker molecules from within the cell. Here, the release of a recently established class of intracellular nucleic acid-based cancer biomarkers—microRNAs (miRNAs)—by high intensity focused ultrasound (HIFU) was investigated in a rat prostate cancer model. The benefits of three different HIFU treatment protocols causing localized tissue lysis (histotripsy), bubble-induced reversible permeabilization (cavitation), or mild hyperthermia in stimulation of miRNA release were compared to untreated controls.

Methods: Copenhagen rats were implanted subcutaneously on the hind limb with the syngeneic MatLyLu prostate cancer cell line. HIFU exposures at 1.1 MHz, optimized for either partial lysis of the tumor tissue or sublethal heating thereof ($I_{SPPA}$=120 W/cm$^2$, 50% duty cycle, 1-minute exposure) were performed in two groups of animals (n=8) after the tumor reached 12 mm in diameter. The control group received sham exposure. Lysis of the tumor tissue was performed using boiling-histotripsy, in which boiling is induced in several milliseconds at the transducer focus by a high amplitude nonlinear HIFU pulse, and the interaction of the boiling bubble with HIFU field leads to tissue emulsification. Blood withdrawals were performed before and immediately after each exposure, and at several post treatment points: 30 minutes, 1, 3 and 24 hours. Specimens were immediately processed into plasma (the cell-free, liquid portion of blood prevented from coagulating), from which miRNA was extracted. Prospective tumor-specific biomarkers were identified by qRT-PCR array profiling of 375 known miRNAs (microRNA Ready-to-Use PCR Panel I, Exiqon) in the cell line, filtering away those known to be broadly expressed in normal tissue or abundant in untreated rat plasma.

Results: The number of copies of tumor-specific miRNAs (miR-34c, miR-9, miR-129-5p, miR-100, miR-196a) were substantially increased (2-fold to 34-fold) within 15 minutes after HIFU-induced tumor lysis or HIFU-induced cavitation of the tumor tissue, but not after HIFU-induced mild hyperthermia. This increase returned to baseline within 1-3 hours. The concentration of a broadly expressed miR-16 was used as a negative control and did not change significantly.

This study demonstrates that HIFU-induced localized tissue lysis may be used to enhance the diagnostic yield of the tumor-specific nucleic acid biomarkers, and thus serve as a "non-invasive biopsy" of undiagnosed tissue masses. Furthermore, these data demonstrate that HIFU-induced cavitation of tumor tissue may be used to enhance the diagnostic yield of the tumor-specific nucleic acid biomarkers, and thus serve as a "non-invasive biopsy" of undiagnosed tissue masses without common patient risks associated with the histotripsy HIFU regime used to induce localized tissue lysis.

Example 3

An experiment to determine the effect of HIFU frequency on the lesion shape and size using repetitive millisecond boiling caused by shock wave heating was performed ex vivo using bovine liver tissue. An acrylic water tank at room temperature (20° C.) was filled with purified water that was degassed using a multiple pinhole degasser to 25% of saturation, as measured by a dissolved oxygen meter (WTW Oxi 330i, Weilheim, Germany). The HIFU source used in the majority of the experiments was a single-element, air-backed, custom-built piezoceramic transducer of 2.158 MHz frequency, 44 mm aperture, and focal length (f-number=1). The transducer was driven by a function generator (Agilent 33250A, Agilent, Palo Alto, CA) and a rf amplifier (300 W, ENI A-300, ENI, Rochester, NY). In addition, two other HIFU transducers with frequencies of 1.1 and 3.4 MHz were used in a small set of experiments to investigate the effect of frequency on the resulting tissue damage. The 1.1 MHz source (also 44 mm aperture and focal length) was driven by a separate rf amplifier (1000 W, RFG-1000, JJ&A Instruments, Duvall, WA). The 3.4 MHz transducer (H-102 model, outer aperture 64 mm and focal length 62.6 mm, Sonic Concepts, Bothell, WA) was driven with the same electronics as the 2 MHz source. A timing board (NI 6608, National Instruments, Austin, TX) was used to trigger the function generator for various pulsing protocols and was controlled using a custom Labview program (National Instruments, Austin, TX). The HIFU source was attached to a three-axis positioning system (Velmex Inc., Bloomfield, NY) to align the focus with the desired position within the exposure sample. B-mode ultrasound imaging was performed during experiments using an HDI-1000 scanner with a CL10-5 scanhead (Philips Medical Systems, Bothell, WA). The excitation voltage at the HIFU source was monitored using a 10× Lecroy high-voltage probe in parallel with the HIFU transducer. The voltage was recorded using a digital oscilloscope (LT344, Lecroy, Chestnut Ridge, NY) and fluctuations in the rms voltage were used to indicate the onset of boiling at the focus. The fluctuations in the voltage are caused by transduction of ultrasound energy that is backscattered from boiling bubbles at the focus. A high-speed camera (Fastrax APX-RS, Photron, San Diego, CA) was used simultaneously with the ultrasound imaging system for viewing heating effects and bubbles in transparent gel phantoms. The camera was operated at a pixel resolution of 1024×1024 and a Nikon 105 mm lens (Nikon, Melville, NY, USA) was used with a bellows extension to obtain a field of view of 10 mm×10 mm (10 µm/pixel). The frames were recorded at 20,000 frames per second (fps) with a 4 µs shutter speed.

Gel phantoms were prepared using polyacrylamide with 7% bovine serum albumin (BSA). These gels are optically transparent and have similar acoustic properties to tissue except for the attenuation coefficient, which is about three times lower than most tissues (0.15 dB/cm/MHz). Localized heating of the gels causes the BSA to denature and form an opaque region above temperatures of about 60° C. that can be visualized optically. To prepare the samples, the liquid mixture of gel constituents was degassed for 1 h in a desiccant chamber, then poured into a custom mold and polymerized. A 1 mm needle was attached to the mold and placed within the gel for alignment purposes. Tissue samples were prepared from bovine heart or liver tissue. The tissue was obtained from an abattoir on the same day as experiments and stored in phosphate buffered saline and on ice until experiments were performed. The tissue was cut into samples to fit in a custom-designed tissue holder (8 cm wide by 8 cm tall by 2.7 cm deep) and was degassed for 1 h in a desiccant chamber immediately prior to experiments. The heart tissue samples were oriented so that the ultrasound was incident perpendicularly to the muscle fibers. For positioning the HIFU focus at a depth of 12 mm within the sample, a removable "pointer" was attached to the transducer before each exposure. The pointer was also used to position the ultrasound imaging probe so that the HIFU axis was aligned with the B-mode imaging plane. After exposures, the tissue was sectioned and photographed to observe the lesion morphology.

For gel phantoms, a fiber-optic probe hydrophone of 100 µm diameter and 100 MHz bandwidth (FOPH 2000, RP Acoustics, Leutenbach, Germany) was embedded at the depth of the HIFU focus in the gel before polymerization. Pressure waveforms were measured at increasing source power levels at the spatial maximum of the peak positive pressure. Measured waveforms were deconvolved using the FOPH impulse response provided by the manufacturer and the sensitivity of the FOPH was corrected to account for the slightly different acoustical properties of gel as compared to water.

Sonications were performed using 1.06, 2.158, and 3.42 MHz transducers. The transducers were operated to produce approximately the same peak positive and negative pressure levels in water as measured with the FOPH. For the 2 MHz transducer, the corresponding power setting was the same as for exposure 3. The equivalent in situ pressure level for each transducer was generated by varying the depth of focus location within the tissue to account for the increase in attenuation with frequency; therefore, the focus was positioned 20, 12, and 6 mm below the tissue surface for the 1, 2, and 3 MHz transducers.

The exposure parameters at the focus were the same for all three exposures: the in situ focal pressure was $p^+=74$ MPa, $p^-=13$ MPa, the duty factor was 0.01, and the total HIFU on time was 500 ms. The pulse duration used in all of these experiments was approximately three times longer than the time to initiate boiling for each frequency: 20 ms (1 MHz), 10 ms (2 MHz), and 5 ms (3 MHz).

Figure 4A:
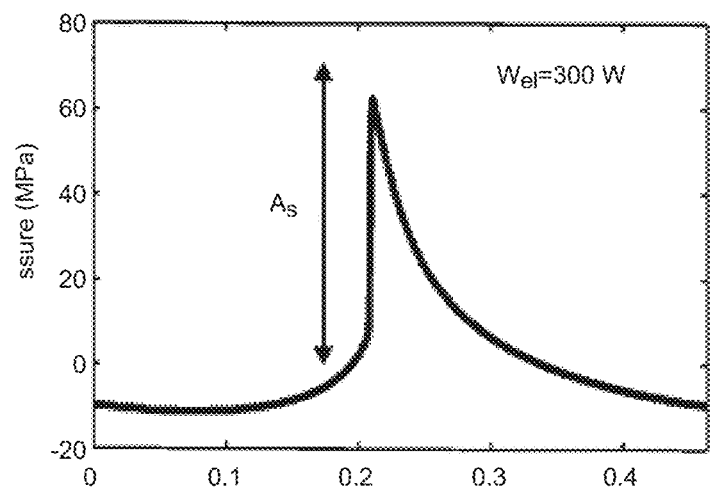
FIG. 4A is a representation of a histotripsy HIFU waveform according to one embodiment of the present technology.
Figure 4B:
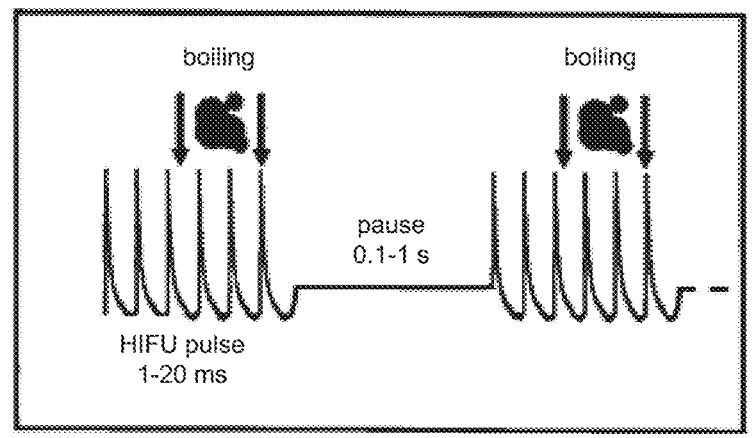
FIG. 4B is a representation of a histotripsy HIFU regime for causing release of a biomarker from a tissue mass according to one embodiment of the present technology.
Figure 4C:
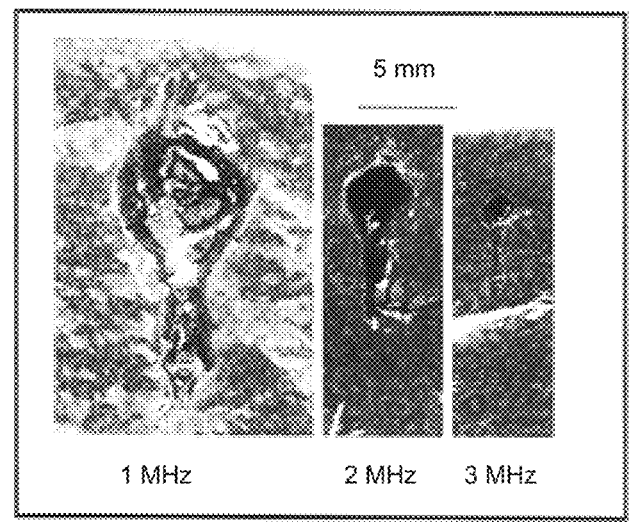
FIG. 4C shows cavities formed in bovine liver tissue when the histotripsy HIFU regime of FIG. 4B is applied ex vivo at 1 MHz, 2 MHz and 3 MHz.
Figure 5A:
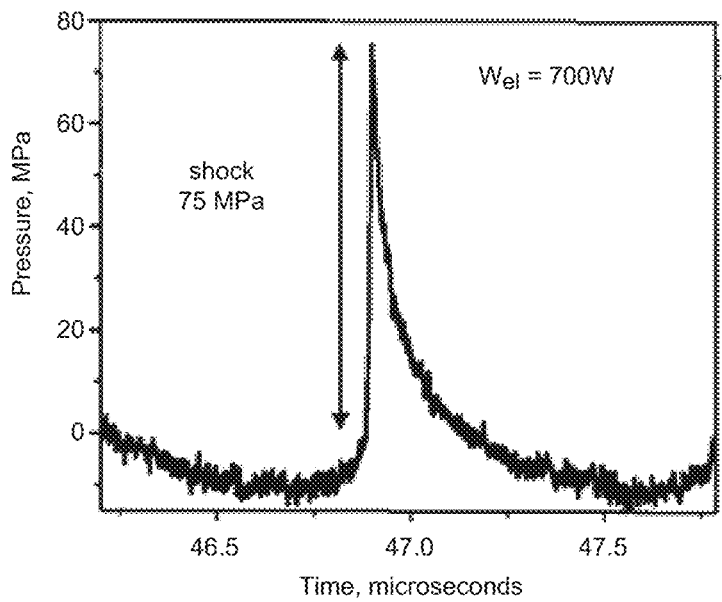
FIG. 5A is a representation of a boiling histotripsy waveform measured in deaerated water according to one embodiment of the present technology.
Figure 5B:
FIG. 5B shows a B-mode monitoring image of tissue being treated with the boiling histotripsy waveform of FIG. 5A with a pulse duration of 1 ms at 1 MHz and for a treatment duration of 30 seconds.
Figure 6:
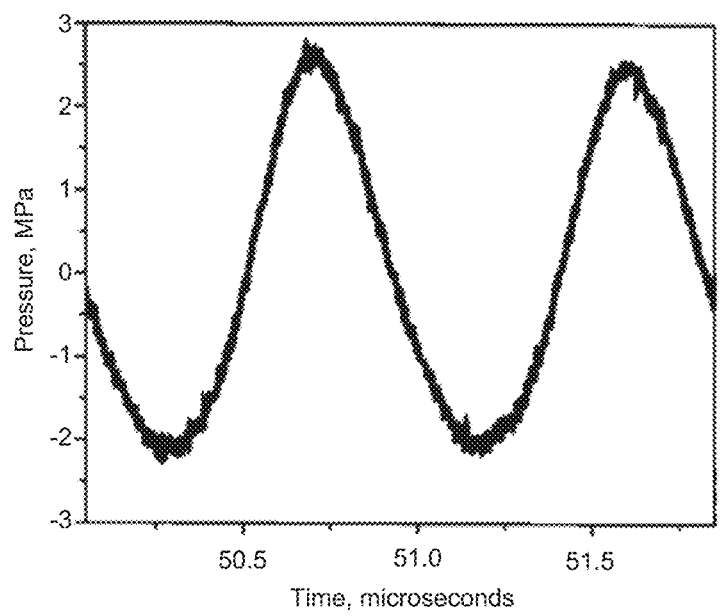
FIG. 6 is a representation of a mild thermal (heating) HIFU waveform measured in deaerated water according to one embodiment of the present technology.

FIG. 4A shows a portion of a histotripsy HIFU waveform; FIG. 4B shows a series of histotripsy HIFU waveforms used to induce boiling in bovine liver tissue to release of a biomarker from a tissue mass according to one embodiment of the present technology. As shown in FIG. 4C, the histotripsy HIFU energy induces cavities in the bovine liver tissue of decreasing size when the frequency of the histotripsy HIFU wave increases from 1.1 MHz, 2.158 MHz and 3.4 MHz.

Example 4

In order to determine if ultrasound stimulation is sufficient for the release of intercellular biomarkers, Copenhagen rats bearing MatLyLu subcutaneous tumors were surgically modified with jugular vein catheters for simplified, repeatable, clean blood draws. HIFU was applied to the modified rats using various regimes shown in Table 2 µsing a 1.5 MHz transducer, under B-mode guidance, in tank of water.

TABLE 2

HIFU regimes for rat model studies.

| Treatment type | $p^+$, MPa | $p^-$, MPa | $T_p$, ms | PRF, Hz | Time/ spot, s |
| --- | --- | --- | --- | --- | --- |
| Liquification (histotripsy) | 90 | 17 | 10 | 1 | 30 |
| Permeabilization (cavitation) | 78 | 16 | 1 | 1 | 30 |
| Mild heating (thermal) | 2.5 | 2.3 | 2 | 250 | 30 |

The modified rats were divided into three separate HIFU treatment groups, according to the ultrasound regimen utilized for treatment: liquification (histotripsy N=11), mild heating (thermal, N=9) and permeabilization (cavitation, N=6), in addition to a mock-treated control group (which did receive anesthesia and other manipulations inherent to the protocol but no ultrasound exposure, N=9). Blood was collected immediately prior to treatment and over a subsequent time course (up to 24 hours).

Prospective tumor-specific biomarkers were identified by qRT-PCR array profiling (Exiqon) of RNA extracts derived from the grafted cell line and untreated rat plasma. miRNAs that were abundant in untreated rat plasma were filtered from the list of those detected in the cell line (Table 1). To control the pre-analytic variability encountered in plasma due to blood cell contaminants introduced during plasma processing, miRNA biomarker candidates were then filtered against a list of miRNAs known to be abundant in blood cells. This process identified miRNAs miR-9, miR-34c, miR-100, miR-129, and miR-196a as putative, tumor-specific miRNAs in this system.

As shown in FIGS. 7A-7E, the abundances of tumor-specific miRNAs in the plasma (miR-9, miR-34c, miR-100, miR-129, miR-196a) were markedly increased within 15 minutes after HIFU-induced liquification (histotripsy) and HIFU-induced tumor cell lysis (permeabilization), but not after HIFU-induced hyperthermia (thermal) or in mock-treated control rats (mock). The concentration of the broadly expressed, non-tissue specific miR-16 was not commensurately increased in HIFU-treated or in control animals (FIG. 7F), indicating that the increase in plasma miRNA abundance was specific and not global.

FIGS. 8A-8F show relative copies of the miRNAs on a shorter time scale than FIGS. 7A-7F. As shown in FIG. 8A-8E, peak release of miR-9, miR-34c, miR-100, miR-129 and miR-196a occurs within just a few minutes of application of the liquification (histotripsy) HIFU.

These data indicate that liquification (histotripsy) HIFU and permeabilization (cavitation) HIFU, but not thermal HIFU, significantly increased prostate cancer biomarker release from prostate tumors in rats.

Further Examples

Example 1. A method of diagnosing a disease or an increased risk of a disease in a subject, the method comprising:
 applying high intensity focused ultrasound (HIFU) energy to a target mass of the subject to cause release of a marker from the mass; and
 thereafter determining a concentration of the marker in a fluid of the subject.

Example 2. The method of Example 1 wherein the disease is a cancer, and wherein the marker is a DNA, an RNA (e.g., an miRNA), a protein or a small molecule.

Example 3. The method of Example 1 or Example 2 further comprising determining that the subject has the disease or the increased risk of the disease if the concentration of the marker in the fluid exceeds a threshold value.

Example 4. The method of Example 3 wherein the threshold value is an amount that is significantly greater than a baseline amount of the marker in fluid determined before applying HIFU energy to the target mass, optionally wherein the threshold value is about 2 times greater than the baseline amount.

Example 5. The method of any one of Examples 1 to 4, wherein applying HIFU energy to a target mass of the subject is non-invasive.

Example 6. The method of any one of Examples 1 to 5 wherein applying HIFU energy to a target mass of the subject comprises inducing cavitation bubble activity in tissue of the target mass Example 7. The method of any one of Examples 1 to 5 wherein applying HIFU energy to a target mass of the subject comprises inducing boiling histotripsy in tissue of the target mass.

Example 8. A method of characterizing two or more masses in a subject, the method comprising:
 optionally determining a baseline concentration of a first marker and/or a second marker in fluid of the subject;
 applying a first high intensity focused ultrasound (HIFU) energy to a first mass of the subject to cause release of a first marker from the mass;
 thereafter determining a concentration of the first marker in a first fluid sample of the subject;
 after a period of time, applying a second HIFU energy to a second mass of the subject to cause release of a second marker from the mass;
 thereafter determining a concentration of the second marker in a second fluid sample of the subject; and
 characterizing the first and second masses based, at least in part, on the concentrations of the first and second markers in the first and second fluid samples, respectively.

Example 9. The method of Example 8 wherein the period of time is sufficient for the concentration of the first marker in fluid of the subject to return to a concentration substantially the same as a baseline concentration of the first marker associated with the fluid before applying the second HIFU energy to the second mass.

Example 10. The method of Example 9 wherein the period of time is no more than about 2 hours.

Example 11. The method of Example 9 wherein the period of time is no more than about 1 hour.

Example 12. The method of Example 9 wherein the period of time is no more than about 20 minutes.

Example 13. The method of any one of Examples 8 to 12 wherein applying the first HIFU energy to the first mass induces boiling histotripsy (e.g. liquification) in the first mass, and applying the second HIFU energy to the second mass induces boiling histotripsy (e.g. liquification) in the second mass.

Example 14. The method of any one of Examples 8 to 12, wherein applying the first HIFU energy to the first mass induces cavitation (e.g., permeabilization) in the first mass, and applying the second HIFU energy to the second mass induces cavitation (e.g., permeabilization) in the second mass.

Example 15. A method of treating a target tissue mass in a subject, the method comprising:
   optionally determining a baseline concentration of a biomarker in a fluid sample of the subject;
   performing a procedure on the target tissue mass of the subject;
   applying high intensity focused ultrasound (HIFU) energy to the target tissue mass;
   determining a concentration of the biomarker in a fluid sample of the subject after applying HIFU energy to the target tissue mass; and
   repeating the performing, applying, and determining until a concentration of the biomarker in the fluid sample falls below a threshold value.

Example 16. The method of Example 15 wherein a period of time between applying HIFU energy to the target tissue mass and determining the concentration of the predetermined biomarker is no more than about 2 hours.

Example 17. The method of Example 15 wherein a period of time between applying HIFU energy to the target tissue mass and determining the concentration of the predetermined biomarker is no more than about 1 hour.

Example 18. The method of Example 15 wherein a period of time between applying HIFU to the target tissue mass and determining the concentration of the predetermined biomarker is no more than about 20 minutes.

Example 19. A method of treating two or more tissue masses in a subject, the method comprising:
   (a) optionally determining a baseline concentration of a first marker and/or second marker in fluid of the subject;
   (b) performing a first procedure on a first tissue mass of the subject;
   (c) applying high intensity focused ultrasound (HIFU) energy to the first tissue mass to cause a first marker to release from the first tissue mass;
   (d) thereafter, determining a concentration of the first marker in a first fluid sample of the subject;
   (e) after a first period of time, performing a second procedure on a second tissue mass of the subject;
   (f) applying HIFU energy to the second tissue mass to cause a second marker to release from the second tissue mass;
   (g) thereafter, determining a concentration of the second marker in a second fluid sample of the subject; and
   (h) after a second period of time, repeating:
      (1) steps (b) to (d) if the concentration of the first marker exceeds a first threshold value;
      (2) steps (e) to (g) if the concentration of the second marker exceeds a second threshold value; or
      (3) steps (b) to (g) if the concentration of the first marker exceeds the first threshold value and the concentration of the second marker exceeds the second threshold value.

Example 20. The method of Example 19 wherein the first threshold value is significantly greater than the baseline concentration of the first marker in fluid of the subject determined before step (c), optionally wherein the threshold value is about 2 times greater than the baseline concentration of the first marker.

Example 21. The method of Example 19 or Example 20 wherein the second threshold value is significantly greater than the baseline concentration of the second marker in fluid of the subject determined before step (f), optionally wherein the threshold value is about 2 times greater than the baseline concentration of the second marker.

Example 22. The method of any one of Examples 19 to 21 wherein applying HIFU energy to the first mass and applying HIFU energy to the second tissue mass induces boiling histotripsy or cavitation.

Example 23. The method of any one of Examples 19 to 22 wherein the fluid sample is obtained from the subject while applying HIFU energy to the subject.

Example 24. A method of inducing release of a marker from target tissue of a subject, the method comprising non-invasively applying high intensity focused ultrasound (HIFU) energy to the target tissue.

Example 25. The method of Example 24 wherein the target tissue is a tumor and the marker is an miRNA.

Example 26. The method of Example 24 or Example 25 wherein a maximum amount of the marker is released from the target tissue in no more than about 5 minutes after application of the HIFU energy.

Example 27. The method of Example 24 or Example 25 wherein a maximum amount of the marker is released from the target tissue in no more than about 3 minutes after application of the HIFU energy.

Example 28. The method of Example 26 or Example 27 wherein the marker is released into a fluid of a subject, and the amount of the marker released from the target tissue is determined by determining a concentration of the marker in a fluid of the subject, wherein the fluid is optionally selected from the group consisting of blood (e.g., fluid and/or non-fluid fractions or derivatives of blood such as whole blood, cells, plasma, serum, microvesicles, and/or cryoprecipitate), plasma, serum, subcellular vesicles, lymph fluid, ascites, urine, cerebrospinal fluid, seminal fluid, breast milk, breast secretions, breast aspirates, and feces.

Example 29. The method of Example 28 wherein the fluid is blood, a blood fraction, or a blood derivative.

Example 30. The method of Example 26 or Example 27 wherein the maximum amount of the marker is significantly greater than the baseline amount of the marker in the fluid before application of the HIFU energy, optionally at least about 2 times greater than the baseline amount.

Example 31. The method of any one of Examples 8 to 13 and 19 to 23 wherein the first marker and the second marker are the same.

Example 32. The method of any preceding Example wherein the marker comprises SEQ ID NO:1.

Example 33. The method of any preceding Example wherein the marker comprises SEQ ID NO:2.

Example 34. The method of any preceding Example wherein the marker comprises SEQ ID NO:3.

Example 35. The method of any preceding Example wherein the marker comprises SEQ ID NO:4.

Example 36. The method of any preceding Example wherein the marker comprises SEQ ID NO:5.

Example 37. The method of any preceding Example wherein the marker comprises SEQ ID NO:6.

Example 38. The method of any preceding Example wherein the subject is human.

Example 39. The method of any preceding Example wherein the subject is a non-human animal.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

We claim:

1. A system for treating a human patient, the system comprising:
   an ultrasound source configured to deliver high intensity focused ultrasound energy to a target tissue mass of the patient;
   a function generator operably coupled to the ultrasound source, wherein the function generator initiates a pulsing protocol for delivering the high intensity focused ultrasound energy from the ultrasound source to the target tissue mass; and
   a controller in communication with the ultrasound source and the function generator, wherein controller is configured to perform operations comprising—
      applying high intensity focused ultrasound energy having a pulse average intensity of between 25 kW/cm$^2$ and 60 k W/cm$^2$ to generate shock waves that induce cavitation in the target tissue mass, the shock waves having a peak positive amplitude of between 78 MPa and 100 MPa, and wherein the cavitation induced by the shock waves causes a biomarker to be released from within cells of the patient;
      comparing (a) a baseline concentration of the biomarker from a first fluid sample of the patient to (b) a concentration of the biomarker in a second fluid sample of the subject within 1 hour after applying high intensity focused ultrasound energy to the target tissue mass; and
      repeating the applying and comparing until the concentration of the biomarker in the second fluid sample falls below a threshold value.

2. The system of claim 1 wherein a period of time between applying high intensity focused ultrasound energy and comparing a baseline concentration of the biomarker in the first fluid sample to the concentration of the biomarker in the second fluid sample is no more than 20 minutes.

3. The system of claim 1 wherein applying high intensity focused ultrasound energy to induce cavitation in the target tissue mass comprises inducing cavitation bubbles that reversibly permeabilize the cells.

4. The system of claim 1 wherein the threshold value of the biomarker is greater than the baseline concentration of the biomarker in the first fluid sample before applying the high intensity focused ultrasound energy, and wherein the threshold value is at least 2 times greater than the baseline concentration.

5. The system of claim 1 wherein the biomarker comprises any one of SEQ ID NO: 1, SEQ ID NO:2, SEQ ID NO:3, SEQ ID NO:4, SEQ ID NO:5, or SEQ ID NO:6.

6. The system of claim 1 wherein the biomarker is released into a fluid of the patient, and wherein the fluid is selected from the group consisting of blood, a blood fraction, a blood derivative, a fluid fraction of blood, a non-fluid fraction of blood, whole blood, blood cells, microvesicles, cryoprecipitate, plasma, serum, subcellular vesicles, lymph fluid, ascites, urine, cerebrospinal fluid, seminal fluid, breast milk, breast secretions, breast aspirates, and feces.

7. The system of claim 1 wherein the fluid of the first and second fluid samples is blood, a blood fraction, or a blood derivative.

8. The system of claim 1 wherein the ultrasound source is configured to deliver high intensity focused ultrasound energy to the target tissue mass of the subject to induce boiling histotripsy in the target tissue mass.

9. The system of claim 1 wherein the biomarker is associated with a disease.

10. The system of claim 9 wherein the disease is a cancer, and wherein the biomarker is a DNA, a RNA, a protein, or a small molecule.

11. A method, comprising:
   determining a baseline concentration of a biomarker in a first fluid sample of a subject;
   applying high intensity focused ultrasound nonlinear waveform energy having a pulse-average intensity of between 25 kW/cm$^2$ and 60 kW/cm$^2$ to generate shock waves that induce cavitation in a target tissue mass of the subject, the shock waves having a peak positive amplitude of between 78 MPa and 100 MPa, and wherein the cavitation induced by the shock waves causes the biomarker to be released from within cells of the target tissue mass;
   determining a second concentration of the biomarker in a second fluid sample of the subject within 1 hour after applying high intensity focused ultrasound nonlinear waveform energy to the target tissue mass; and
   repeating the applying the high intensity focused ultrasound nonlinear waveform energy and determining the second concentration of the biomarker, until the second concentration of the biomarker in the second fluid sample falls below a threshold value.

12. The method of claim 11 wherein the target tissue mass is a tumor and the biomarker is a miRNA.

13. The method of claim 11 wherein the amount of the biomarker released from within the cells of the target tissue mass is determined by determining a concentration of the biomarker in a fluid of the subject, wherein the fluid is selected from the group consisting of blood, a blood fraction, a blood derivative, a fluid fraction of blood, a non-fluid fraction of blood, whole blood, blood cells, microvesicles, cryoprecipitate, plasma, serum, subcellular vesicles, lymph fluid, ascites, urine, cerebrospinal fluid, seminal fluid, breast milk, breast secretions, breast aspirates, and feces.

14. The method of claim 11 wherein the threshold value of the biomarker is greater than the baseline concentration of the biomarker in the first fluid sample before applying the high intensity focused ultrasound nonlinear waveform energy, and wherein the threshold value is at least 2 times greater than the baseline concentration.

15. The method of claim 11 wherein a period of time between applying high intensity focused ultrasound nonlinear waveform energy to the target tissue mass and determining the second concentration of the biomarker is no more than 20 minutes.

16. The method of claim 11 wherein the applying high intensity focused ultrasound nonlinear waveform energy is at a pulse repetition frequency of 1 Hz.

17. The method of claim 11 wherein the biomarker is associated with a disease.

18. The method of claim 17 wherein the disease is a cancer, and wherein the biomarker is a DNA, a RNA, a protein, or a small molecule.

* * * * *

SEQUENCE LISTING

```
Sequence total quantity: 6
SEQ ID NO: 1           moltype = RNA  length = 23
FEATURE                Location/Qualifiers
source                 1..23
                       mol_type = genomic RNA
                       organism = Rattus norvegicus
SEQUENCE: 1
tctttggtta tctagctgta tga                                              23

SEQ ID NO: 2           moltype = RNA  length = 22
FEATURE                Location/Qualifiers
source                 1..22
                       mol_type = genomic RNA
                       organism = Rattus norvegicus
SEQUENCE: 2
taggtagttt catgttgttg gg                                               22

SEQ ID NO: 3           moltype = RNA  length = 23
FEATURE                Location/Qualifiers
source                 1..23
                       mol_type = genomic RNA
                       organism = Rattus norvegicus
SEQUENCE: 3
aggcagtgta gttagctgat tgc                                              23

SEQ ID NO: 4           moltype = RNA  length = 21
FEATURE                Location/Qualifiers
source                 1..21
                       mol_type = genomic RNA
                       organism = Rattus norvegicus
SEQUENCE: 4
cttttgcgg tctgggcttg c                                                 21
```

```
SEQ ID NO: 5          moltype = RNA  length = 22
FEATURE               Location/Qualifiers
source                1..22
                      mol_type = genomic RNA
                      organism = Rattus norvegicus
SEQUENCE: 5
aacccgtaga tccgaacttg tg                                                  22

SEQ ID NO: 6          moltype = RNA  length = 22
FEATURE               Location/Qualifiers
source                1..22
                      mol_type = genomic RNA
                      organism = Rattus norvegicus
SEQUENCE: 6
tagcagcacg taaatattgg cg                                                  22
```